(12) United States Patent
Shin et al.

(10) Patent No.: US 11,970,732 B2
(45) Date of Patent: Apr. 30, 2024

(54) METHOD FOR DETERMINING NUCLEIC ACID QUALITY OF BIOLOGICAL SAMPLE

(71) Applicants: GENCURIX INC., Seoul (KR); LOGONE BIO CONVERGENCE RESEARCH FOUNDATION, Seoul (KR)

(72) Inventors: Young Kee Shin, Seoul (KR); Jin Ju Kim, Seoul (KR); Sung Su Kim, Seoul (KR); Hyun Jeung Choi, Seoul (KR); Young Ho Moon, Seoul (KR); Myung Sun Kim, Seoul (KR); Jee Eun Kim, Seoul (KR)

(73) Assignees: GENCURIX INC., Seoul (KR); LOGONE BIO CONVERGENCE RESEARCH FOUNDATION, Seoul (KR)

(*) Notice: Subject to any disclaimer, the term of this patent is extended or adjusted under 35 U.S.C. 154(b) by 0 days.

(21) Appl. No.: 16/500,549

(22) PCT Filed: Apr. 4, 2018

(86) PCT No.: PCT/KR2018/003992
§ 371 (c)(1),
(2) Date: Oct. 3, 2019

(87) PCT Pub. No.: WO2018/186687
PCT Pub. Date: Oct. 11, 2018

(65) Prior Publication Data
US 2020/0102595 A1    Apr. 2, 2020

(30) Foreign Application Priority Data

Apr. 4, 2017  (KR) .................. 10-2017-0043918

(51) Int. Cl.
*C12Q 1/68* (2018.01)
*C12Q 1/686* (2018.01)
(52) U.S. Cl.
CPC .................................. *C12Q 1/686* (2013.01)
(58) Field of Classification Search
None
See application file for complete search history.

(56) References Cited

U.S. PATENT DOCUMENTS 10,337,072 B2 * 7/2019 Hudson ..................... A01H 1/04
2018/0051325 A1 * 2/2018 Litterst ................. C07K 14/721

FOREIGN PATENT DOCUMENTS

| CN | 102597272 A | 7/2012 |
| CN | 104560697 A | 4/2015 |
| JP | 2002281977 A | 10/2002 |
| JP | 2008048668 A | 3/2008 |
| JP | 2011517573 A | 6/2011 |
| JP | 2012504426 A | 2/2012 |
| WO | 2011/060240 A1 | 5/2011 |

OTHER PUBLICATIONS

Rajasekaran et al. Employing digital droplet PCR to detect BRAF and V600E mutations in formalin-fembedded reference standard cell lines. Journal of Visuallized Experiments, vol. 104, e53190, p. 1-8, 2015.*
Cao et al. Droplet digital PCR for simultaneous quantification of general and human associated fecal indicators for water quality assessment. WaterResearch, vol. 70, p. 33-349, 2015.*
Kim et al. Droplet digital PCR-based EGFR mutation detection with internal quality control index to determine the quality of DNA. Scientific Reports, vol. 8:534, p. 1-10, Jan. 2018.*
Cao et al. (Water Research, 2015, vol. 70, 337-349, 2075, with supplementary materials attached) (Year: 2015).*
Rajasekaran et al. (Journal of Visualized Experiments, vol. 104, 653190, p. 1-8, 2015) (Year: 2015).*
Roberts et al. (Journal of Clinical Microbiology, 2013, 51(7):2195-2203) (Year: 2013).*
Moy, Christopher et al., "Mutation and copy number detection in human cancers using a custom genotyping assay", Genomics 98 (2011) 296-301.
International Search Report dated Jul. 16, 2018, issued in PCT/KR2018/003992, with English translation.
Kim, Sung-Su et al., "Droplet digital PCR-based EGFR mutation detection with an internal quality control index to determine the quality of DNA", Scientific Reports (2018) 8:543 DOI:10.1038/s41598-017-18642-x, (10 pages).
Machine English Translation of Specification and Claims of JP 2002281977 A, 21 pp.
Machine English Translation of CN 102597272 A, 43 pp.

* cited by examiner

*Primary Examiner* — Stephanie K Mummert
(74) *Attorney, Agent, or Firm* — CANTOR COLBURN LLP

(57) ABSTRACT

The present invention relates to a method for determining the DNA quality of a biological sample and, more specifically, to a method for determining the DNA quality of a biological sample by performing a quantitative polymerase chain reaction (PCR) using primers capable of amplifying a target gene, a method for preparing the primers used in the method, and a method for standardizing the amount of detected target gene mutation by using the determined DNA quality. The method of the present invention enables objective evaluation of the DNA quality of a biological sample used in gene analysis and the presentation of objective results on the expression ratio of a gene mutation, thereby providing reliable information in the fields of clinical research and companion diagnosis.

9 Claims, 13 Drawing Sheets
Specification includes a Sequence Listing.

FIG. 10

| Sample No. | Blood Storage wk | CX Ratio (%) | DIN | Preliminary result | | | | | After Manualization | | | | |
|---|---|---|---|---|---|---|---|---|---|---|---|---|---|
| | | | | cobas EGFR | ddEGFR | ddEGFR | ddEGFR M/W(%) | Sanger | cobas EGFR | ddEGFR | ddEGFR | ddEGFR M/W(%) |
| 1 | 111 | 23 | 3.2 | MND | — | MD | L858R | 0.8 | WT | NA | NA | NA | — |
| 2 | 111 | 51 | 2.2 | MND | — | MD | T790M/G719X | 1.08/1.02 | Invalid | MND | — | Invalid | — |
| 3 | 6 | 41 | 4.6 | MND | — | MD | L858R | 1.57 | WT | MD | L858R | L858R | 2.57 |
| 4 | 6 | 28 | 3.7 | MND | — | MD | G719X | 10.17 | WT | MD | G719X | G719X | 20.17 |
| 5 | 6 | 12 | 3.9 | MND | — | MD | L858R | 5.91 | WT | MD | L858R | L858R | 4.55 |
| 6 | 6 | 15 | 3.1 | MND | — | MD | L858R | 7.4 | WT | NA | NA | NA | — |
| 7 | 3 | 45 | 4.4 | MND | — | MD | 20Ins | 12.88 | WT | MND | — | Ex20ins | 7.4 |
| 8 | 3 | 34 | 4.1 | MND | — | MD | 19del | 15.72 | WT | MD | 19del | 19del | 3.15 |

FIG. 11
A
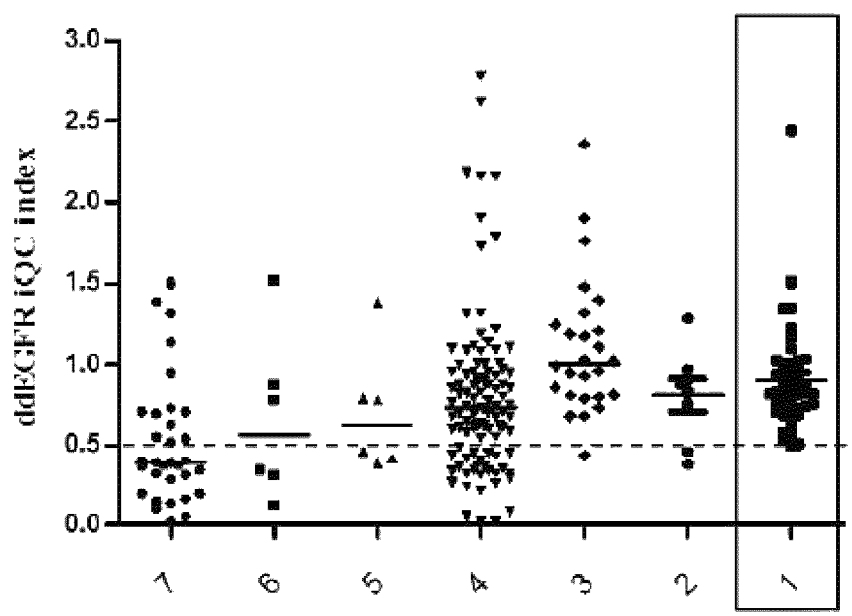
B
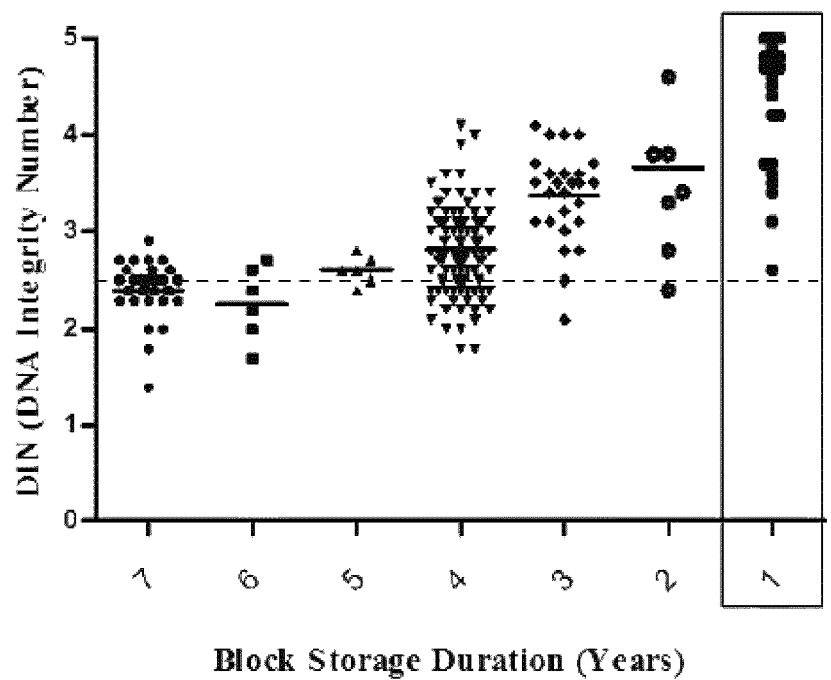
Block Storage Duration (Years)

SEQUENCE LISTING

```
<160> NUMBER OF SEQ ID NOS: 2

<210> SEQ ID NO 1
<211> LENGTH: 10
<212> TYPE: DNA
<213> ORGANISM: homo sapiens

<400> SEQUENCE: 1
ttaagagaag                                                              10

<210> SEQ ID NO 2
<211> LENGTH: 11
<212> TYPE: DNA
<213> ORGANISM: Homo sapiens

<400> SEQUENCE: 2
ccagcgtgga t                                                            11
```

METHOD FOR DETERMINING NUCLEIC ACID QUALITY OF BIOLOGICAL SAMPLE

INCORPORATION-BY-REFERENCE OF MATERIAL SUBMITTED ELECTRONICALLY

Incorporated by reference in its entirety herein is a computer-readable nucleotide/amino acid sequence listing submitted herewith and identified as follows: 643 bytes ASCII file named "SWF0006US_ST25.txt" created Mar. 1, 2024.

TECHNICAL FIELD

The present application claims priority from Korean Patent Application No. 10-2017-0043918, filed on Apr. 4, 2017, the entire content of which is incorporated herein by reference.

The present invention relates to a method for determining nucleic acid quality of a biological sample, more specifically, to primers capable of amplifying the internal quality control region; or a method to determine nucleic acid quality of a biological sample by performing PCR (polymerase chain reaction) using a set of primers or probes, the primers used in the method; or a method for preparing a set of primers or probes and a method for standardizing a mutations rate of a target gene applying thus determined nucleic acid quality.

BACKGROUND OF THE INVENTION

It is becoming increasingly common for clinicians to analyze the molecular characteristics of a disease before selecting the most appropriate treatment for a given disease. Providing an optimal treatment to patients together with clinically relevant and accurate companion diagnostics (CDx) is becoming a way to maximize the therapeutic effect for a disease.

In July 2011, the US Food and Drug Administration issued guidelines for use of the companion diagnostics (CDx) as an important tool to guide the selection and use of appropriate treatment modalities (In vitro companion diagnostics devices—guidance for industry and FDA staff, US FDA, 2014). According to this definition, CDx analysis is a very important in vitro diagnostic tool that provides the information needed for the safe and effective use of therapeutic drugs. The FDA has also clearly identified three areas in which CDx analysis is required: [a] the area of selecting patients in which a particular treatment is expected to have the greatest effect, [b] the area of selecting patients highly possible to suffer from the serious side effects as a result of a treatment with a particular treatment and [c] the area of increasing safety and efficacy of a drug by monitoring treatment responses and modulating the treatment regimen (e.g., drug dosage, treatment time, etc.).

The purpose of CDx is to apply the properties of specific molecules to obtain the required therapeutic outcome by thoroughly understanding the mechanisms of molecular physiological etiology and drug action.

On the other hand, there is a need for a method that allows very robust and accurate analysis in a short period of time if any specific drug and its dosage needs to be tailored to an individual by CDx. At this time, important factors to consider include standardization of analytical methods, verification of reagents and methods, and participation of proven laboratory experience and pathologists. However, recent studies regarding quality assurance of biological samples, conducted to verify the mutational state of the standard tumor panel, have shown that different results may be obtained in different laboratories carrying out the study despite the use of the same or similar methods.

Detailed analysis conditions may be different depending on the agency performing the genetic analysis. Furthermore, differences in the state and quality of a sample to be analyzed can affect the test results. Therefore, It is becoming very important to quantify and standardize the quality of a sample to analyze in order to minimize such variables.

DETAILED DESCRIPTION OF THE INVENTION

Technical Problem

Accordingly, the inventors of the present invention objectively evaluated the state of the genes extracted from a biological sample obtained from an individual, and made a reasonable effort to develop a method to secure the reliability of a gene analysis result. As a result, primers for PCR capable of specifically amplifying the internal quality control region satisfying the predetermined conditions; or a method of objectively evaluating the quality of nucleic acids in a biological sample using a set of primers and probes were developed, thereby completing the present invention.

Accordingly, an aspect of the present invention is to provide a method for determining a nucleic acid quality of a biological sample, the method comprising the steps of:
(a) extracting a nucleic acid from a biological sample obtained from a subject;
(b) performing PCR on the extracted nucleic acids with i) primers; or ii) a set of primers and a probe which are capable of amplifying the internal quality control region;
(c) calculating a copy number of the internal quality control region from the result of the PCR;
(d) calculating the internal quality control index (iQC index) according to the following equation:

Internal control quality index=the copy number of the internal quality control region/the copy number of input DNA of the PCR; and (e) determining that the nucleic acid quality of the sample is appropriate in case where the internal control quality index is equal to or higher than a predetermined threshold, or determining that the nucleic acid quality of the sample is better as the internal control quality index becomes closer to 1.

Another aspect of the present invention is to provide a method for preparing i) primers or ii) a set of primers and a probe,
(a) designing i) primers or ii) a set of primers and a probe which are capable of amplifying nucleic acid fragments of the internal quality control region;
(b) performing PCR on the nucleic acids contained in the reference standard material with the primers or the set of the primers and the probes;
(c) calculating the copy number of the internal quality control region from the result of PCR; and
(d) selecting primers of which [the copy number of the internal quality control region detected/the copy number of input DNA of the reference standard material] is 0.90 to 1.10.

Another aspect of the present invention is to provide a method for calculating the % mutation index of a target gene in a biological sample, the method comprising the steps of:

(a) extracting nucleic acids from a biological sample obtained from a subject;
(b) performing the first PCR on the extracted nucleic acids with i) primers or ii) a set of primers and a probe which are capable of amplifying an internal quality control region;
(c) calculating a copy number of the internal quality control region from the result of the first PCR;
(d) performing a second PCR on the extracted nucleic acids with iii) primers or iv) a set of primers and a probe which are capable of amplifying a target gene or mutation site;
(e) calculating the copy number of the target gene or the mutation site from the result of the second PCR; and
(f) calculating the % mutation index according to the following equation:

% Mutation index=the copy number of the target gene or mutation site/the copy number of the internal quality control region×100.

Another aspect of the present invention is to provide a method for standardizing a mutation frequency of a target gene or a mutation site in a biological sample, the method comprising the steps of:
(a) measuring a mutational frequency of a target gene or mutation site in a biological sample; and
(b) calculating a standardized mutation frequency by dividing the measured mutation frequency by the internal quality control index of the sample.

Technical Solution

An embodiment according to an aspect of the present invention provides a method for determining a nucleic acid quality of a biological sample, the method comprising the steps of:
(a) extracting nucleic acids from a biological sample obtained from a subject;
(b) performing PCR on the extracted nucleic acids with i) primers; or ii) a set of primers and a probe which are capable of amplifying the internal quality control region;
(c) calculating a copy number of the internal quality control region from the result of the PCR;
(d) calculating the internal quality control index (iQC index) according to the following equation:

Internal control quality index=the copy number of the internal quality control region/the copy number of input DNA of the PCR; and (e) determining that the nucleic acid quality of the sample is appropriate in case where the internal control quality index is equal to or higher than a predetermined threshold, or determining that the nucleic acid quality of the sample is better as the internal control quality index becomes closer to 1.

An embodiment according to another aspect of the present invention provides a method for preparing i) primers or ii) a set of primers and a probe,
(a) designing i) primers or ii) a set of primers and a probe which are capable of amplifying nucleic acid fragments of the internal quality control region;
(b) performing PCR on the nucleic acids contained in the reference standard material with the primers or the set of the primers and probes;
(c) calculating a copy number of the internal quality control region from the result of PCR; and
(d) selecting primers of which [the copy number of the internal quality control region detected/the copy number of input DNA of the reference standard substance] is 0.90 to 1.10.

An embodiment according to another aspect of the present invention provides a method for calculating the % mutation index of a target gene in a biological sample, the method comprising the steps of:
(a) extracting nucleic acids from a biological sample obtained from a subject;
(b) performing the first PCR on the extracted nucleic acids with i) primers or ii) a set of primers and a probe which are capable of amplifying the internal quality control region;
(c) calculating a copy number of the internal quality control region from the result of the first PCR;
(d) performing the second PCR on the extracted nucleic acids with iii) primers or iv) a set of primers and a probe which are capable of amplifying a target gene or mutation site;
(e) calculating the copy number of the target gene or the mutation site from the result of the second PCR; and
(f) calculating the % mutation index according to the following equation:

% Mutation index=the copy number of the target gene or mutation site/the copy number of the internal quality control region×100.

An embodiment according to another aspect of the present invention provides a method for standardizing a mutational frequency of a target gene or mutation site in a biological sample, the method comprising the steps of:
(a) measuring the mutational frequency of a target gene or mutation site in a biological sample; and
(b) calculating a standardized mutation frequency by dividing the measured mutation frequency by the internal quality control index of the sample.

Hereinafter, the present invention will be described in detail.

The present invention provides a method for determining a nucleic acid quality of a biological sample, the method comprising the steps of:
(a) extracting nucleic acids from a biological sample obtained from a subject;
(b) performing PCR on the extracted nucleic acids with i) primers; or ii) a set of primers and a probe which are capable of amplifying the internal quality control region;
(c) calculating a copy number of the internal quality control region from the result of the PCR;
(d) calculating the internal quality control index (iQC index) according to the following equation:

Internal control quality index=the copy number of the internal quality control region/the copy number of input DNA of the PCR; and (e) determining that the nucleic acid quality of the sample is appropriate in case where the internal control quality index is equal to or higher than a predetermined threshold, or determining that the nucleic acid quality of the sample is better as the internal control quality index becomes closer to 1.

In modern medicine, genes obtained from biological samples are becoming useful sources of information in studying the pathological mechanisms of diseases or in diagnosing the pathological conditions of patients through companion diagnostics. In the gene amplification techniques for this kind of analysis, the quality of gene the biological samples of interest plays a very important role for successful molecular assays after gene amplification.

However, biological samples used for gene amplification often fail to maintain their original state after going through a series of processing steps such as collection, storage, and analysis. For example, in case of blood-circulating tumor cells, cell death happens very frequently in the course of obtaining a sample, and it is known that genome DNA is fragmented into small pieces during caspase-mediated cell death. In case of formalin-fixed, paraffin-embedded tissue (FFPE-T), which is the most commonly used storage form of biological samples in clinical studies and molecular diagnosis of diseases, although it has the advantage of being able to maintain the tissue in the best condition for immunohistochemical analysis, it can cause irreversible damages such as gene fragmentation, chemical modification, cross-linking, methylation, oxidative stress, etc. as the storage period prolongs.

When analysis is performed using these genes with various types of damages, it is not only impossible to obtain accurate research results, but also fatal errors directly related to life may occur in serious matters such as diagnosis of diseases. Nonetheless, this fact is often overlooked in clinical research and diagnostics, and in most cases, the internal controls contained in the various types of commercially available assay kits are used for the purpose of verifying whether the analysis process itself is normally performed, not for evaluating the status or quality of genes in the biological sample.

The method of the present invention relates to a method for determining the quality of nucleic acids of a biological sample to be analyzed in the entire fields of clinical research and diagnostics which include a process of analyzing genes contained in a biological sample.

More specifically, the present invention relates to a method for determining whether a biological sample maintains nucleic acid quality sufficient to yield objective or meaningful experimental results when used in the analytical techniques of direct gene analysis such as real-time PCR, digital PCR, genome sequencing, pyrosequencing, next generation sequencing, etc.

In the present invention, the "nucleic acid quality" of the biological sample means the amount of genomic DNA contained in the biological sample, the presence or absence of contaminants, the size of genomic DNA, whether DNA is segmented or bases are damaged, whether there is cross-linking, amplification efficacy, the content of amplifiable target gene fragments, etc. Preferably, it means the extent to which the target gene to detect or analyze or the target gene containing mutations maintains integrity as an amplifiable template in the biological sample. Mostly preferably, it means the extent to which the region containing mutations within the target gene maintains integrity.

The results of numerous molecular screenings and analysis methods often depend on the overall quality of the genomic DNA (gDNA). For example, Array CGH (aCGH) and next generation sequencing (NGS) may require undamaged, high quality gDNA to ensure results. It is advisable to perform quality control (QC) of input data (samples, etc.) for such workflows, especially for expensive methods such as NGS. This can save time and effort wasted on low quality samples.

Similar to the iQC index of the present invention, the DNA integrity number (DIN) and the RNA integrity number (RIN) index are also numerical values representing the integrity of nucleic acids. Measurements can be made, for example, using a commercially available measuring instrument (Bioanalyzer, Agilent 2200 Tapestation, 4200 Tapestation, etc.), which is actually a gel running based analysis. Therefore, although the experimental method itself is simple, the reliability of the result can not be guaranteed compared with the amplifiable nucleic acid measurement by the actual PCR methods. Furthermore, additional equipment and consumables are needed as opposed to the method of verifying the integrity of nucleic acids simultaneously in the PCR step for the detection of mutations.

According to one embodiment of the present invention, the present inventors have found that the copy numbers of the internal quality control region within EGFR exons 18 to 21 were less than 50% of those of input DNA in 166 biological samples which account for more than half of the entire samples after evaluating the gene quality of exon 18 to 21 of epidermal growth factor receptor in a total of 316 FFPE samples obtained from non-small cell lung cancer (NSCLC) patients. Considering that mutations which are important indicators for determining therapeutic drugs for NSCLC patients occur primarily in EGFR exon 18 to 21, it means that the reliability of the mutation analysis results of the 166 biologic samples could not be guaranteed, suggesting that the "nucleic acid quality" of the biological samples was not appropriate for the genetic analysis to detect mutations in EGFR exon 18 to 21.

Hereinafter, each step of the nucleic acid quality determination method will be described in more detail.

Step (a) extracting a nucleic acid from a biological sample obtained from a subject;

In the present invention, the "biological sample" refers to one or more selected from the group consisting of a cell line obtained from a subject, a histological slide, a biopsy specimen, a formalin-fixed paraffin-embedded (FFPE) tissue, body fluid, feces, urine, plasma, serum, whole blood, isolated blood cells, and cells isolated from blood. Preferably, it may be one or more selected from the group consisting of the cell line, a biopsy specimen, a FFPE tissue, isolated blood cells and cells isolated from blood, and more preferably, at least one selected from the group consisting of a biopsy specimen, a FFPE tissue and cells isolated from blood, and most preferably, it may be a FFPE tissue. The biological sample may contain analyzable nucleic acids.

After a biopsy, the tissue obtained from a patient is usually fixed with formalin (formaldehyde) or the like. The fixed sample tissue is dehydrated and embedded in a solid support such as paraffin to produce FFPE tissue. Nucleic acids in the FFPE sample, especially DNA, are present in the fixed cells and are either fragmented or cross-linked by formalin, therefore it is necessary to remove the paraffin and lyse the fixed cells to release DNA and other nucleic acids from the cells.

In the present invention, the term "paraffin" comprehensively refers to an embedding medium of a biological sample used in all types of analysis including morphological, immunohistochemical and enzyme-histochemical analysis. That is, the paraffin in the present invention may be a simple petroleum-based paraffin wax alone, or may include all different kinds of components which can be added to the embedding medium for the purposes such as quality improvement etc. on the petroleum paraffin base. Herein, the petroleum paraffin wax refers to a mixture of hydrocarbons derived from petroleum, which are in a solid state at room temperature.

In the present invention, the term "individual" means a healthy individual or a living organism suspected of having any diseases or subject to research. Generally, the entity may be a human. However, the subject can also be animals including mammals such as agricultural animals including rodents (including mice, rats, hamsters and guinea pigs), cats, dogs, rabbits, cows, horses, goats, sheep, pigs and the like, and primates (including monkeys, chimpanzees, orangutans and gorillas). The "individual" in the present invention may be a human that needs treatments or diagnosis of a disease.

In the present invention, the term "nucleic acid" includes not only single-stranded and double-stranded DNA but also RNA complements thereof. Examples of DNA include, but not limited to, genomic DNA, cDNA corresponding to the genomic DNA, DNA amplified by PCR, and their combinations, and hybrids of DNA and RNA. Preferably, the nucleic acid may be fragmented genomic DNA.

In the present invention, the nucleic acid extraction can be performed without limitation as long as it is a commonly used method in the art. For example, phenol/chloroform extraction or SDS extraction (Tai et al., Plant Mol. Biol. Reporter 8: 297-303, 1990), or CTAB extraction method (Cetyl Trimethyl Ammonium Bromide; Murray et al., Nuc. Res., 4321-4325, 1980) or any commercially available nucleic acid extraction kits can be used.

In one embodiment of the present invention, the FFPE-treated specimen was sectioned with the thickness of 5 to 10 μm using a rotary microtome, then mixed with a buffer designed for extraction from FFPE (FFPE buffer, VERSANT tissue preparation reagents, Box 1, Siemens) followed by incubation at 80° C. for 30 minutes.

The FFPE sample can be cut using a microtome for easy contact with reagents and control of the amount of the FFPE samples. The section thickness is preferably, but not limited to, 5 to 15 μm. Sectioned FFPE samples are placed in an extraction tube for DNA, especially for genomic DNA, and treated with proteinases to degrade and fragment proteins in the sample. In the present invention, the proteinase is preferably protease K, and protease K treatment is carried out preferably for 20 to 40 minutes at 45 to 70° C., more preferably for 25 to 35 minutes at 60 to 65° C., and most preferably for 30 minutes at 65° C. Treatment in the settings below the lower limit of the above conditions results in a lower efficiency of proteolytic degradation and ultimately reduces the DNA isolation efficiency. Treatment in the settings over the upper limit of the above conditions results in a reduced DNA isolation efficiency due to DNA degradation during the separation process as well as reduced productivity due to increased overall isolation time.

Proteins or cell debris may be removed from the treated sample, and the genomic DNA may be obtained, for example, by treating RNA degrading enzyme to remove RNA and isolate the genomic DNA.

These procedures can be carried out with commercially available kits and devices, for example, the tissue preparation system of Siemens and the associated reagents (VERSANT tissue preparation reagents).

Step (b) performing PCR on the extracted nucleic acid with i) primers; or ii) a set of primers and a probe which are capable of amplifying the internal quality control region;

In the present invention, the term "internal quality control region" indicates in the extracted nucleic acids
  i) a certain region within the target gene to be analyzed or a certain region within the gene containing a mutation site; or
  ii) a region adjacent to the target gene or the mutation site to be analyzed.

The internal quality control region may be located within a target gene to detect (intron, exon, or a region including all of them) or in a gene including a mutation site (intron, exon, or a region including all of them).

In addition, the internal quality control region may be located adjacent to the target gene or the mutation site, and preferably, in the "adjacent region" in the 5'- or 3'-direction from the target gene or mutation site (also referred to as a hotspot), preferably within 20 kb (kilobase), within 19 kb, within 18 kb, within 17 kb, within 16 kb, within 15 kb, within 14 kb, within 13 kb, within 12 kb, 11 kb within 10 kb, within 9 kb, within 8 kb, within 7 kb, within 6 kb, within 5 kb, within 4 kb, within 3 kb, within 2 kb, within 1 kb, within 900 bases, within 800 bases, within 700 bases, within 600 bases, within 500 bases, within 400 bases, within 300 bases, within 200 bases, within 100 bases. In the present invention, the distance is measured based on genetic information of the wild-type genomic DNA. In the present invention, it is understood that the distance is rounded to one decimal place for 1 kb to 20 kb, and rounded to ten decimal place for less than 1 kb.

The "adjacent region" is i) preferably set such that the target gene to detect and the reference site are placed as close as possible in order to reduce the influence of the copy number variation which is a characteristic of cancer cells, and ii) it is possible to improve the detection accuracy with the small fragmented nucleic acids extracted from the FFPE or the like by setting it close to the hot spot with high mutation frequency. Preferably, the "certain region in the gene" and the "adjacent region" are those in which SNPs (single nucleotide polymorphism) are not frequent, that is, they are found with the frequency of less than 5%, preferably less than 1%, more preferably less than 0.5%.

In addition, if there are two or more sites where mutations occur, they may be regions in the middle of these mutation sites (in the middle of the two mutation sites at both ends).

Two or more internal quality control regions can be applied for PCR when the mutation sites are sufficiently separated from each other (for example, over 20 kb) or when two or more internal quality control regions are to be established for one mutation site. The following iQC indexes for two or more internal quality control regions may be calculated by averaging each result, or independently evaluating the iQC index to determine nucleic acid quality. In this case, the average may be calculated by an arithmetic mean, a geometric mean, a harmonic mean, a power mean, a weighted arithmetic mean, or a combination thereof.

In one embodiment of the present invention, the internal quality control region was selected within exons 18-21 of epidermal growth factor receptor (EGFR).

When the internal quality control is determined inadequately, it is possible to generate inaccurate copy numbers and frequencies due to changes in the wild-type and mutated sequence populations induced by frequent fragmentation of nucleic acids. When the internal quality control region is selected from the different chromosome from those of the target nucleic acid region or the site where the mutation occurs, incorrect copy numbers may be derived from a biological sample in which copy number variation occurs frequently such as cancer cells.

For example, in one embodiment of the present invention, the internal quality control region exists within the exon 18 to 21 region of EGFR gene with the distance of about 7.5 kb from the exon 18 end, and about 11 kb from the exon 21 end. Meanwhile, the internal quality control region in the embodiment of the present invention is about 25 kb away from the position of exon 28, and such distance is inappropriate as an internal quality control region of the present invention.

The "target gene" to be analyzed in the present invention includes, for example, a marker gene used in identifying genes or distinguishing individuals, a marker gene used for diagnosis of diseases, a marker gene having a genetically significant mutation, a marker gene having a short tandem repeat (STR) and a marker gene having a single nucleotide polymorphism, etc. "Target gene" may contain a mutation or may be wild-type, but preferably be a marker gene comprising a mutation which is genetically or diagnostically meaningful, and more preferably a marker comprising a diagnostically important mutation.

The "target gene" in the present invention may be, but is not limited hereto, one of those listed in the following Table 1 (Transcription ID indicates Genbank Accession No.):

TABLE 1

| Gene Name | Transcript ID |
|---|---|
| ABL1 | NM_005157 |
| ACVR1 | NM_001111067 |
| AGO2 | NM_012154 |
| AKT1 | NM_001014431 |
| AKT2 | NM_001626 |
| AKT3 | NM_005465 |
| ALK | NM_004304 |
| ALOX12B | NM_001139 |
| AMER1 | NM_152424 |
| ANKRD11 | NM_013275 |
| APC | NM_000038 |
| AR | NM_000044 |
| ARAF | NM_001654 |
| ARID1A | NM_006015 |
| ARID1B | NM_020732 |
| ARID2 | NM_152641 |
| ARID5B | NM_032199 |
| ASXL1 | NM_015338 |
| ASXL2 | NM_018263 |
| ATM | NM_000051 |
| ATR | NM_001184 |
| ATRX | NM_000489 |
| AURKA | NM_003600 |
| AURKB | NM_004217 |
| AXIN1 | NM_003502 |
| AXIN2 | NM_004655 |
| AXL | NM_021913 |
| B2M | NM_004048 |
| BABAM1 | NM_001033549 |
| BAP1 | NM_004656 |
| BARD1 | NM_000465 |
| BBC3 | NM_001127240 |
| BCL10 | NM_003921 |
| BCL2 | NM_000633 |
| BCL2L1 | NM_138578 |
| BCL2L11 | NM_138621 |
| BCL6 | NM_001706 |
| BCOR | NM_001123385 |
| BIRC3 | NM_182962 |
| BLM | NM_000057 |
| BMPR1A | NM_004329 |
| BRAF | NM_004333 |
| BRCA1 | NM_007294 |
| BRCA2 | NM_000059 |
| BRD4 | NM_058243 |
| BRIP1 | NM_032043 |
| BTK | NM_000061 |
| CALR | NM_004343 |
| CARD11 | NM_032415 |
| CARM1 | NM_199141 |
| CASP8 | NM_001080125 |
| CBFB | NM_022845 |
| CBL | NM_005188 |
| CCND1 | NM_053056 |
| CCND2 | NM_001759 |
| CCND3 | NM_001760 |
| CCNE1 | NM_001238 |
| CD274 | NM_014143 |
| CD276 | NM_001024736 |

TABLE 1-continued

| Gene Name | Transcript ID |
|---|---|
| CD79A | NM_001783 |
| CD79B | NM_001039933 |
| CDC42 | NM_001791 |
| CDC73 | NM_024529 |
| CDH1 | NM_004360 |
| CDK12 | NM_016507 |
| CDK4 | NM_000075 |
| CDK6 | NM_001145306 |
| CDK8 | NM_001260 |
| CDKN1A | NM_078467 |
| CDKN1B | NM_004064 |
| CDKN2Ap14ARF | NM_058195 |
| CDKN2Ap16INK4A | NM_000077 |
| CDKN2B | NM_004936 |
| CDKN2C | NM_078626 |
| CEBPA | NM_004364 |
| CENPA | NM_001809 |
| CHEK1 | NM_001274 |
| CHEK2 | NM_007194 |
| CIC | NM_015125 |
| CREBBP | NM_004380 |
| CRKL | NM_005207 |
| CRLF2 | NM_022148 |
| CSDE1 | NM_001242891 |
| CSF1R | NM_005211 |
| CSF3R | NM_000760 |
| CTCF | NM_006565 |
| CTLA4 | NM_005214 |
| CTNNB1 | NM_001904 |
| CUL3 | NM_003590 |
| CXCR4 | NM_003467 |
| CYLD | NM_001042355 |
| CYSLTR2 | NM_020377 |
| DAXX | NM_001141970 |
| DCUN1D1 | NM_020640 |
| DDR2 | NM_006182 |
| DICER1 | NM_030621 |
| DIS3 | NM_014953 |
| DNAJB1 | NM_006145 |
| DNMT1 | NM_001379 |
| DNMT3A | NM_022552 |
| DNMT3B | NM_006892 |
| DOT1L | NM_032482 |
| DROSHA | NM_013235 |
| DUSP4 | NM_001394 |
| E2F3 | NM_001949 |
| EED | NM_003797 |
| EGFL7 | NM_201446 |
| EGFR | NM_005228 |
| EIF1AX | NM_001412 |
| EIF4A2 | NM_001967 |
| EIF4E | NM_001130678 |
| ELF3 | NM_004433 |
| EP300 | NM_001429 |
| EPAS1 | NM_001430 |
| EPCAM | NM_002354 |
| EPHA3 | NM_005233 |
| EPHA5 | NM_004439 |
| EPHA7 | NM_004440 |
| EPHB1 | NM_004441 |
| ERBB2 | NM_004448 |
| ERBB3 | NM_001982 |
| ERBB4 | NM_005235 |
| ERCC2 | NM_000400 |
| ERCC3 | NM_000122 |
| ERCC4 | NM_005236 |
| ERCC5 | NM_000123 |
| ERF | NM_006494 |
| ERG | NM_182918 |
| ERRFI1 | NM_018948 |
| ESR1 | NM_001122740 |
| ETV1 | NM_001163147 |
| ETV6 | NM_001987 |
| EZH1 | NM_001991 |
| EZH2 | NM_004456 |
| FAM175A | NM_139076 |
| FAM46C | NM_017709 |
| FAM58A | NM_152274 |

TABLE 1-continued

| Gene Name | Transcript ID |
|---|---|
| FANCA | NM_000135 |
| FANCC | NM_000136 |
| FAT1 | NM_005245 |
| FBXW7 | NM_033632 |
| FGF19 | NM_005117 |
| FGF3 | NM_005247 |
| FGF4 | NM_002007 |
| FGFR1 | NM_001174067 |
| FGFR2 | NM_000141 |
| FGFR3 | NM_000142 |
| FGFR4 | NM_213647 |
| FH | NM_000143 |
| FLCN | NM_144997 |
| FLT1 | NM_002019 |
| FLT3 | NM_004119 |
| FLT4 | NM_182925 |
| FOXA1 | NM_004496 |
| FOXL2 | NM_023067 |
| FOXO1 | NM_002015 |
| FOXP1 | NM_001244814 |
| FUBP1 | NM_003902 |
| FYN | NM_153047 |
| GATA1 | NM_002049 |
| GATA2 | NM_032638 |
| GATA3 | NM_002051 |
| GLI1 | NM_005269 |
| GNA11 | NM_002067 |
| GNAQ | NM_002072 |
| GNAS | NM_000516 |
| GPS2 | NM_004489 |
| GREM1 | NM_013372 |
| GRIN2A | NM_001134407 |
| GSK3B | NM_002093 |
| H3F3A | NM_002107 |
| H3F3B | NM_005324 |
| H3F3C | NM_001013699 |
| HGF | NM_000601 |
| HIST1H1C | NM_005319 |
| HIST1H2BD | NM_021063 |
| HIST1H3A | NM_003529 |
| HIST1H3B | NM_003537 |
| HIST1H3C | NM_003531 |
| HIST1H3D | NM_003530 |
| HIST1H3E | NM_003532 |
| HIST1H3F | NM_021018 |
| HIST1H3G | NM_003534 |
| HIST1H3H | NM_003536 |
| HIST1H3I | NM_003533 |
| HIST1H3J | NM_003535 |
| HIST2H3C | NM_021059 |
| HIST2H3D | NM_001123375 |
| HIST3H3 | NM_003493 |
| HLA-A | NM_001242758 |
| HLA-B | NM_005514 |
| HNF1A | NM_000545 |
| HOXB13 | NM_006361 |
| HRAS | NM_001130442 |
| IGOSLG | NM_015259 |
| ID3 | NM_002167 |
| IDH1 | NM_005896 |
| IDH2 | NM_002168 |
| IFNGR1 | NM_000416 |
| IGF1 | NM_001111285 |
| IGF1R | NM_000875 |
| IGF2 | NM_001127598 |
| IKBKE | NM_014002 |
| IKZF1 | NM_006060 |
| IL10 | NM_000572 |
| IL7R | NM_002185 |
| INHA | NM_002191 |
| INHBA | NM_002192 |
| INPP4A | NM_001134224 |
| INPP4B | NM_001101669 |
| INPPL1 | NM_001567 |
| INSR | NM_000208 |
| IRF4 | NM_002460 |
| IRS1 | NM_005544 |
| IRS2 | NM_003749 |
| JAK1 | NM_002227 |
| JAK2 | NM_004972 |
| JAK3 | NM_000215 |
| JUN | NM_002228 |
| KDM5A | NM_001042603 |
| KDM5C | NM_004187 |
| KDM6A | NM_021140 |
| KDR | NM_002253 |
| KEAP1 | NM_203500 |
| KIT | NM_000222 |
| KLF4 | NM_004235 |
| KMT2A | NM_001197104 |
| KMT2B | NM_014727 |
| KMT2C | NM_170606 |
| KMT2D | NM_003482 |
| KNSTRN | NM_033286 |
| KRAS | NM_033360 |
| LATS1 | NM_004690 |
| LATS2 | NM_014572 |
| LMO1 | NM_002315 |
| LYN | NM_002350 |
| MALT1 | NM_006785 |
| MAP2K1 | NM_002755 |
| MAP2K2 | NM_030662 |
| MAP2K4 | NM_003010 |
| MAP3K1 | NM_005921 |
| MAP3K13 | NM_004721 |
| MAP3K14 | NM_003954 |
| MAPK1 | NM_002745 |
| MAPK3 | NM_002746 |
| MAPKAP1 | NM_001006617 |
| MAX | NM_002382 |
| MCL1 | NM_021960 |
| MDC1 | NM_014641 |
| MDM2 | NM_002392 |
| MDM4 | NM_002393 |
| MED12 | NM_005120 |
| MEF2B | NM_001145785 |
| MEN1 | NM_000244 |
| MET | NM_000245 |
| MGA | NM_001164273 |
| MITF | NM_198159 |
| MLH1 | NM_000249 |
| MPL | NM_005373 |
| MRE11A | NM_005591 |
| MSH2 | NM_000251 |
| MSH3 | NM_002439 |
| MSH6 | NM_000179 |
| MSI1 | NM_002442 |
| MSI2 | NM_138962 |
| MST1 | NM_020998 |
| MST1R | NM_002447 |
| MTOR | NM_004958 |
| MUTYH | NM_001128425 |
| MYC | NM_002467 |
| MYCL1 | NM_001033082 |
| MYCN | NM_005378 |
| MYD88 | NM_002468 |
| MYOD1 | NM_002478 |
| NBN | NM_002485 |
| MCOA3 | NM_181659 |
| NCOR1 | NM_006311 |
| NEGR1 | NM_173808 |
| NF1 | NM_001042492 |
| NF2 | NM_000268 |
| NFE2L2 | NM_006164 |
| NFKBIA | NM_020529 |
| NKX2-1 | NM_001079668 |
| NKX3-1 | NM_006167 |
| NOTCH1 | NM_017617 |
| NOTCH2 | NM_024408 |
| NOTCH3 | NM_000435 |
| NOTCH4 | NM_004557 |
| NPM1 | NM_002520 |
| NRAS | NM_002524 |
| NSD1 | NM_022455 |
| NTHL1 | NM_002528 |
| NTRK1 | NM_002529 |

TABLE 1-continued

| Gene Name | Transcript ID |
|---|---|
| NTRK2 | NM_006180 |
| NTRK3 | NM_001012338 |
| NUF2 | NM_031423 |
| NUP93 | NM_014669 |
| PAK1 | NM_002576 |
| PAK7 | NM_177990 |
| PALB2 | NM_024675 |
| PARK2 | NM_004562 |
| PARP1 | NM_001618 |
| PAX5 | NM_016734 |
| PBRM1 | NM_018313 |
| PDCD1 | NM_005018 |
| PDCD1LG2 | NM_025239 |
| PDGFRA | NM_006206 |
| PDGFRB | NM_002609 |
| PDPK1 | NM_002613 |
| PGR | NM_000926 |
| PHOX2B | NM_003924 |
| PIK3C2G | NM_004570 |
| PIK3C3 | NM_002647 |
| PIK3CA | NM_006218 |
| PIK3CB | NM_006219 |
| PIK3CD | NM_005026 |
| PIK3CG | NM_002649 |
| PIK3R1 | NM_181523 |
| PIK3R2 | NM_005027 |
| PIK3R3 | NM_003629 |
| PIM1 | NM_002648 |
| PLCG2 | NM_002661 |
| PLK2 | NM_006622 |
| PMAIP1 | NM_021127 |
| PMS1 | NM_000534 |
| PMS2 | NM_000535 |
| PNRC1 | NM_006813 |
| POLD1 | NM_002691 |
| POLE | NM_006231 |
| PPARG | NM_015869 |
| PPM1D | NM_003620 |
| PPP2R1A | NM_014225 |
| PPP4R2 | NM_174907 |
| PPP6C | NM_002721 |
| PRDM1 | NM_001198 |
| PRDM14 | NM_024504 |
| PREX2 | NM_024870 |
| PRKAR1A | NM_212471 |
| PRKCI | NM_002740 |
| PRKD1 | NM_002742 |
| PTCH1 | NM_000264 |
| PTEN | NM_000314 |
| PTP4A1 | NM_003463 |
| PTPN11 | NM_002834 |
| PTPRD | NM_002839 |
| PTPRS | NM_002850 |
| PTRRT | NM_133170 |
| RAB35 | NM_006861 |
| RAC1 | NM_018890 |
| RAC2 | NM_002872 |
| RAD21 | NM_006265 |
| RAD50 | NM_005732 |
| RAD51 | NM_002875 |
| RAD51B | NM_133509 |
| RAD51C | NM_058216 |
| RAD51D | NM_133629 |
| RAD52 | NM_134424 |
| RAD54L | NM_001142548 |
| RAF1 | NM_002880 |
| RARA | NM_000964 |
| RASA1 | NM_002890 |
| RB1 | NM_000321 |
| RBM10 | NM_001204468 |
| RECQL | NM_032941 |
| RECQL4 | NM_004260 |
| REL | NM_002908 |
| RET | NM_020975 |
| RFWD2 | NM_022457 |
| RHEB | NM_005614 |
| RHOA | NM_001664 |
| RICTOR | NM_152756 |
| RIT1 | NM_006912 |
| RNF43 | NM_017763 |
| ROS1 | NM_002944 |
| RPS6KA4 | NM_003942 |
| RPS6KB2 | NM_003952 |
| RPTOR | NM_020761 |
| RRAGC | NM_022157 |
| RRAS | NM_006270 |
| RRAS2 | NM_012250 |
| RTEL1 | NM_032957 |
| RUNX1 | NM_001754 |
| RXRA | NM_002957 |
| RYBP | NM_012234 |
| SDHA | NM_004168 |
| SDHAF2 | NM_017841 |
| SDHB | NM_003000 |
| SDHC | NM_003001 |
| SDHD | NM_003002 |
| SESN1 | NM_014454 |
| SESN2 | NM_031459 |
| SESN3 | NM_144665 |
| SETD2 | NM_014159 |
| SETD8 | NM_020382 |
| SF3B1 | NM_012433 |
| SH2B3 | NM_005475 |
| SH2D1A | NM_002351 |
| SHOC2 | NM_007373 |
| SHQ1 | NM_018130 |
| SLX4 | NM_032444 |
| SMAD2 | NM_001003652 |
| SMAD3 | NM_005902 |
| SMAD4 | NM_005359 |
| SMARCA4 | NM_003072 |
| SMARCB1 | NM_003073 |
| SMARCD1 | NM_003076 |
| SMO | NM_005631 |
| SMYD3 | NM_001167740 |
| SOCS1 | NM_003745 |
| SOS1 | NM_005633 |
| SOX17 | NM_022454 |
| SOX2 | NM_003106 |
| SOX9 | NM_000346 |
| SPEN | NM_015001 |
| SPOP | NM_001007228 |
| SPRED1 | NM_152594 |
| SRC | NM_198291 |
| SRSF2 | NM_003016 |
| STAG2 | NM_001042749 |
| STAT3 | NM_139276 |
| STAT5A | NM_003152 |
| STAT5B | NM_012448 |
| STK11 | NM_000455 |
| STK19 | NM_004197 |
| STK40 | NM_032017 |
| SUFU | NM_016169 |
| SUZ12 | NM_015355 |
| SYK | NM_003177 |
| TAP1 | NM_000593 |
| TAP2 | NM_018833 |
| TBX3 | NM_016569 |
| TCEB1 | NM_005648 |
| TCF3 | NM_001136139 |
| TCF7L2 | NM_001146274 |
| TEK | NM_000459 |
| TERT | NM_198253 |
| TET1 | NM_030625 |
| TET2 | NM_001127208 |
| TGFBR1 | NM_004612 |
| TGFBR2 | NM_001024847 |
| TMEM127 | NM_001193304 |
| TMPRSS2 | NM_001135099 |
| TNFAIP3 | NM_006290 |
| TNFRSF14 | NM_003820 |
| TOP1 | NM_003286 |
| TP53 | NM_000546 |
| TP53BP1 | NM_001141980 |
| TP63 | NM_003722 |
| TRAF2 | NM_021138 |

TABLE 1-continued

| Gene Name | Transcript ID |
|---|---|
| TRAF7 | NM_032271 |
| TSC1 | NM_000368 |
| TSC2 | NM_000548 |
| TSHR | NM_000369 |
| U2AF1 | NM_006758 |
| UPF1 | NM_002911 |
| VEGFA | NM_001171623 |
| VHL | NM_000551 |
| VTCN1 | NM_024626 |
| WHSCl | NM_001042424 |
| WHSC1L1 | NM_023034 |
| WT1 | NM_024426 |
| WWTR1 | NM_001168280 |
| XIAP | NM_001167 |
| XPO1 | NM_003400 |
| XRCC2 | NM_005431 |
| YAP1 | NM_001130145 |
| YES1 | NM_005433 |
| ZFHX3 | NM_006885 |

In the present invention, the "mutation site" (or mutation site) includes, for example, a mutation site of a marker gene used for identifying a gene or distinguishing an individual, a mutation site of a marker gene used for the diagnosis of a specific disease, or a gene having a genetically significant mutation, and preferably the mutation site is significant for each purpose, such as gene identification, individual identification, diagnosis of a particular disease, genetic significance, and the like.

The "mutation" to be analyzed in the present invention may be a mutation in the target gene or a mutation located in the gene listed in the following Table 2 and the corresponding codons, but is not limited thereto:

TABLE 2

| Gene | Codons |
|---|---|
| ABL1 | G250, Q252, Y253, E255, T315, F317, M351, F359, H396R |
| AKT1 | E17, Q124, G171, E170 |
| AKT2 | V140 |
| ALK | K1062, D1091, C1156, M1166, I1171, F1174, L1196, A1234, F1245, I1250, R1275, Y1278 |
| APC | S1234, I1307, E1309, E1317, P1319, G1339, S1341, P1361, P1372, P1373, R1399, S1400, S1407, S1411, V1414, S1415, S1421, T1438, P1439, P1440, T1445, P1453, N1455, E1464, S1465, T1487, L1488, F1491, T1493, E1494, T1537, K1555, T1556, I1557, C1578 |
| AR | T878, T8782, Q581 |
| ARAF | S214 |
| ARID1A | D1850, G2087 |
| ARID2 | R314, S297, R285, A1773 |
| ASXL1 | Y591, E635, G645, G646, E1102D |
| ASXL2 | R591 |
| ATM | D1853, R3008, R3376, E2164 |
| ATRX | K1936, E625 |
| BARD1 | P24 |
| BCL6 | R594, R618 |
| BCOR | N1425, N14591 |
| BRAF | G464, G466, G469, Y472, N581, D594, F595, G596, L597, A598_T599, V600, V600_K601, K601, V60010, K6010, G4694, N5810, G4660 |
| CARD11 | R170 |
| CBL | Y371, L380, C384, C404, R420Q |
| CDH1 | T263 |
| CDK4 | R24 |
| CDKN2A | S43, P48, A57, A68, D74, L78, P81, H83, D84, L97, D108, P114, H831, D1081, P1140 |
| CEBPA | P23, H24, Q83, K304_Q305, E309_T310, Q312_K313, K313_V314, K313_V314, K313, E316_L317, E316_L317insQ |

TABLE 2-continued

| Gene | Codons |
|---|---|
| CHEK2 | K373, K3732 |
| CIC | R215 |
| CREBBP | R1446, S1680, R14460 |
| CRLF2 | F232C |
| CSF1R | Y969C |
| CTCF | R377 |
| CTNNB1 | D32, S33, G34, I35, H36, S37, T40, T41, T42, A43, P44, S45, G48, K49, E53, K335, S376, S334, D324, T412, G349, S455, C619 |
| DICER1 | E1813 |
| DIS3 | R382, D488 |
| DNMT1 | E432 |
| DNMT3A | G543, R635, S714, F731, R882, R8820 |
| DOT1L | G1386 |
| EGFR | R108, A289, G598, R677, E709, G719, K745_E749, K745_E746, E746_A750, E746_S752, E746_T751, E746_E749, E746_T751, L747_P753, L747_A750, L747_T751, L747_S752, L747_T751, L747_E749, L747_, L747_S752_I759, D761, S768, V769_D770, D770_N771, H773_V774, R776, T790, L833, H835, T847, P848, T854, L858, L861, G863, L8587, A2898, R252, R222 |
| EP300 | D1399, D13990, C1164 |
| EPHB1 | R170 |
| ERBB2 | G309, S310, L755, L755_T759del, D769H, D769Y, G776, V777, V842, R869, R678 |
| ERBB3 | V1043, D297, M91 |
| ERBB4 | R711 |
| ERCC2 | D312 |
| ESR1 | D538, Y537, L536, E380, S463, V533 |
| ETV1 | R187 |
| ETV6 | R369 |
| EZH2 | Y646, R690 |
| FBXW7 | G423, R465, R479, R505, S582, R689, R4652, R5054, R4792 |
| FGFR2 | S252, P253, C382, N549, N550, K659 |
| FGFR3 | R248, S249, G370, S371, Y373, G380, A391, K650, G697, S2492, Y3730 |
| FGFR4 | V550 |
| FLT3 | D835, I836, D8358 |
| FOXL2 | C134W |
| FUBP1 | R430 |
| GATA1 | M1, S30, V74I |
| GATA2 | G320, L321, L359, R362Q |
| GNA11 | R183, Q209, R256 |
| GNAQ | R183, Q209 |
| GNAS | R201, Q227, R8448 |
| GRIN2A | R1067 |
| HIST1H3B | E74 |
| HNF1A | W206, P291, G292 |
| HRAS | G12, G13, Q61, E62, Q614, G136, G122 |
| IDH1 | G70, V71, R132, V178, R13239, P33 |
| IDH2 | R140, R172, V294, R1402, R1721 |
| IL7R | K395 |
| IRS2 | G1057 |
| JAK1 | R873 |
| JAK2 | F537_K539, H538_K539, K539, I540_E543, R541_E543, N542_E543, E543_D544, V617, R683 |
| JAK3 | A572, A573, R657Q |
| KDR | S1100, E759 |
| KEAP1 | R470 |
| KIT | D52, D419, Y503_F504, K509, M541, K550_K558, P551_V555, P551_E554, P551_M552, Y553_K558, E554_K558, Q556_V560, W557_K558, W557, W557_V559, W557_E561, W557_V559, K558_E562, K558, K558_V560, V559, V559_V560, V559_E561, V560, E561, Y570_L576, D572, L576, D579, K642, V654, T670, S715, D816, K818, D820, N822, Y823, V825, D8160 |
| KMT2C | V656 |
| KRAS | G10_A11, G12, G13, V14, L19, Q22, T58, A59, Q61, K117, A146, G1242, G133, Q619, A1467 |
| LATS2 | A3243 G3630 |
| MAP2K1 | Q56, K57, D67, P124, P1240, F53, E203 |
| MAP2K4 | R134 |
| MAP3K1 | S1330, S939 |
| MAPK1 | E322 |
| MAX | R600 |

TABLE 2-continued

| Gene | Codons |
|---|---|
| MED12 | L36, Q43, G44, L1224, L12240 |
| MEF2B | D83V |
| MET | T1010, Y1248, Y1253, M1268, K1360 |
| MLL3 | K2797 |
| MPL | S505, W515, W515R |
| MSH6 | F1088, T1219I |
| MTOR | S22152, F1888 |
| MYC | T58 |
| MYCN | P44 |
| MYD88 | S219, S243, L265P |
| NF1 | L844 |
| NFE2L2 | D29, L30, G31, R34, E79, T80, G81, E82, E794, D294, R342 |
| NOTCH1 | L1574, L1575, V1578, L1585, L1586, F1592, L1593, L1594, R1598, R1599, L1600, L1601, L1678, L1679, Q2460, P2514, A1944 |
| NOTCH2 | E385, N463 |
| NPM1 | W288, W290 |
| NRAS | G12, G13, A18, G60, Q61, Q6193, G128, G138 |
| NTRK1 | T264 |
| PAK7 | E144 |
| PARP1 | I562 |
| PAX5 | P80R |
| PDGFRA | V561, S566_E571, N659, D842, I843_D846, D1071N |
| PIK3C2G | S670 |
| PIK3CA | R38, E81, R88, R93, G106, R108, K111, G118, V344, N345, C378, E418, C420, E453, P539, E542, E545, Q546, E547, S553, K567, H701, E726, C901, G1007, Y1021, T1025, M1043, N1044, D1045, A1046, H1047, G1049, T1052, A1066, N1068, E54534, H104715, E54217, Q5467, R887, N3453, C4209, G1187, E7265, E4535, K1113, R932, R382, R1080, E39 |
| PIK3R1 | G376, D560, N564, K567 |
| POLE | P2864, V4111 |
| PPP2R1A | P179, R182, R183, S256, W257, R258, R1832 |
| PREX2 | G233C |
| PTCH1 | P1315 |
| PTEN | K6, P38, L42, H61, Y68, Y76, Y88, H93, I101, C105, L112, H123, A126, G129, R130, C136, A151, Y155, R159, K164, G165, S170, R173, N184, E242, P246, P248, C250, K267, V290, L318, T319, T321, N323, F347, R1309, R1730, K128 |
| PTPN11 | G60, D61, E69, A72, T73, E76, S502, G503, Q510 |
| PTPRD | S431, P666 |
| RAC1 | P295 |
| RAF1 | S2570 |
| RET | E632_T636, E632_L633, C634, M918T |
| RHOA | E40, Y42 |
| RICTOR | S1101 |
| RIT1 | M90 |
| RUNX1 | L56, R107, D198, R201, R204, R162, R205 |
| SDHA | S4560, A466, R465 |
| SF3B1 | E622, R625, H662, K666, K700, K7002 |
| SMAD4 | A118, D351, R361, G386, R3619, D537, P356 |
| SMARCA4 | T910, G1232 |
| SMARCB1 | R377, A382, P383 |
| SMO | W535L |
| SPOP | F133, F1338, W131, F102 |
| SRSF2 | P95, P95_R102, P107H |
| STAG2 | R370 |
| STK11 | D194, P281, F354L |
| TET2 | C25, C262, Q764, F868, R1261, H1380, V1718L |
| TNFAIP3 | L324 |
| TP53 | E11, D49, P82, T102, G105, Y107, R110, L111, F113, K120, T125, Y126, Y126_K132, S127, P128, L130, N131, K132, M133, F134, C135, A138, K139, T140, C141, P142, V143, Q144, L145, V147, S149, P151, P152, P153, G154, T155, R156, V157, R158, A159, M160, A161, I162, Y163, K164, S166, H168, M169, T170, E171, V172, V173, R174, R175, C176, P177, P177_C182, H178, H179, E180, R181, C182, D184, D186, G187, P190, P191, Q192, H193, L194, I195, R196, V197, E198, G199, N200, R202, V203, Y205, D208, R209, T211, F212, R213,, S215, V216, V217, V218, Y220, E224, G226, S227, D228, C229, T230, I232, Y234, N235, Y236, M237, C238, N239, S240, S241, C242, M243, G244, G245, M246, N247, R248, R249, P250, I251, L252, T253, I254, I255, L257, E258, D259, G262, L265, G266, R267, F270, E271, V272, R273, V274, C275, A276, C277, P278, G279, R280, D281, R282, R283, T284, E285, E286, E287, N288, R290, K291, K292, E294, P300, P301, S303, K320, G334, R337, R27328, R24892, R17538, R2820, G2451, Y2202, H1938, H1797, R1583, C1763, P2783, Y1633, R2800, G2660, I1950, S2419, R2499, V1577, C2386, E2856, R3375, G2445, V1733, P1512, C2752, K1321, Y2050, V2720, C1359, D2818, E2718, V2168, M2378, Y2347, E2867, L1946, A1596, R2675, S1275, C2425, Y2364, C1414, F2704, A1613, V2743, S2153, R2132 H2142, R1101, N2390, T1550, P1520, P2500, G1050, L1300, Q136, F109 |
| TP63 | R379 |
| TSC2 | N1515 |
| TSHR | M453, I486, L512, I568, D619, A623, L629, I630, T632, D633, D633E |
| U2AF1 | S34, Q157, S347 |
| VHL | V62, S65, S72, V74, F76, N78, S80, P81, L85, P86, L89, N90, S111, G114, H115, L118, D121, L128, V130, G144, F148, I151, L153, V155, L158, E160, C162, V166, R167, L169, L184 |
| WT1 | V303, R312, A314, R394, D396, R462 |
| XPO1 | E571, R749 |

In the present invention, the "primer" means a single-stranded nucleic acid which can serve as a starting point of the template-directed DNA synthesis under suitable conditions of a suitable temperature and buffer (i.e., the presence of four types of nucleoside triphosphates and polymerases such as DNA polymerase or RNA polymerase or reverse transcriptase). The suitable length of a primer is dependent on the intended use of the primer, but is generally a length comprised of at least 7 nucleotides, more typically a length comprised of 10 to 30 nucleotides. Other primers may be somewhat longer, such as in a length comprised of 30 to 50 nucleotides. PCR primers typically have a length of about 15-30 base pairs, selected to be complementary to the strand upstream (i.e., 5' to 3' orientation) of the target sequence, and to the opposite strand of the downstream strand (i.e., 3' to 5' orientation). The 5' end of the primer defines the end of the amplified PCR product. Primers may contain almost the same amount of GC content as AT content, and can not include a long stretch of one base. In addition, primers should not contain structures that are substantially complementary to each other, which ensures that "primer dimer" or other secondary structures are not formed. Short primer molecules generally require a lower temperature to form a sufficiently stable hybrid complex with the template. Primers need not reflect the exact sequence of the template, but should be complementary enough to be able to hybridize with the template. The "primer site" or "primer binding site" means a segment of the internal quality control region in which the primer is hybridized. The term "primer pair" indicates a set of primers comprising a 5' upstream primer (forward primer) which hybridizes with the complement of the 5' end of the amplified DNA sequence, and a 3' downstream primer (reverse primer) which hybridizes with the 3' end of the amplified DNA.

In the present invention, the term "complementary" means that one nucleic acid is identical to another nucleic acid molecule or hybridizes selectively thereto. The selectivity of the hybridization exists when more selective hybridization occurs than in the complete absence of specificity. Typically, selective hybridization will occur when there is at least about 55% identity, alternatively at least 65%, at least 75%, or at least 90% identity to a site comprised of 14-25 or more nucleotides. In an alternative embodiment, one nucleic acid is specifically hybridized to another nucleic acid. M. Kanehisa, Nucleic Acids Res. 12: 203 (1984) is referred.

In the present invention, the "probe" is a nucleic acid which can bind to the target nucleic acid with complementary sequences by more than one kind of chemical bindings, typically by forming complementary base pairs or typically by forming hydrogen bonds, thereby making a double strand structure (duplex structure). Probes bind to or hybridize to a "probe binding site." Probes may be labeled with a detectable label to allow for easy detection of the probe, particularly once the probe has hybridized to its complementary target. Label attached to the probe may include various labels known in the art to which the present invention belong, for example, which can be detected by chemical or physical means. Labels that may be attached to the probe include, but are not limited hereto, radioactive isotopes, fluorophores, chromophores, gold particles, quantum dots, mass labels, electron dense particles, magnetic particles, spin markers, molecules that release chemiluminescence, electrochemically active molecules, enzymes, cofactors, and enzyme substrates. Probes can vary in size. Some probes are relatively short. Generally, probes can be composed of 7 to 15 nucleotides or more. Other probes may be composed of 20, 30, or more than 40 nucleotides. Another probes are longer and may be composed of 50, 60, 70, 80, 90 or more nucleotides. However, other probes may be even longer and be composed of 100, 150, 200 or more nucleotides. Probes may be of any particular length that falls within the ranges described above.

In the present invention, PCR may be performed using a PCR reaction mixture containing various components known in the art necessary for the PCR reaction. The PCR reaction mixture may contain an appropriate amount of DNA polymerase, dNTP, PCR buffer solution and water (dH$_2$O) in addition to the nucleic acid extract to be amplified, primers and probes. The PCR buffer solution includes Tris-HCl, MgCl$_2$, KCl, etc. At this time, the MgCl$_2$ concentration greatly affects the specificity and yield of amplification, and can be preferably used in the range of 1.5-2.5 mM. Generally, when Mg$^{2+}$ is excessive, non-specific PCR amplification products are increased, and when Mg$^{2+}$ is insufficient, the yield of PCR product is decreased. The PCR buffer solution may further contain an appropriate amount of Triton X-100. Also, PCR may be performed under a general PCR reaction conditions such as pre-denaturing template DNA at 94-95° C., subsequent cycles of denaturation; annealing; and extension, followed by final elongation at 72° C. In the above, denaturation and amplification can be performed at 94-95° C. and 72° C., respectively, and the temperature at the time of binding can be changed depending on the type of the primers, preferably 52-57° C., and more preferably 55° C. Time and number of cycles in each step can be determined according to the conditions commonly practiced in the art.

The nucleic acids amplified by the primers can be detected by electrophoresis on an agarose gel followed by band identification to confirm the presence and relative amount of the amplified product, or can be quantified by detecting fluorescent signals from the primers and probes.

The term "PCR" (polymerase chain reaction) as used in the present invention is widely known in the art, and refers to a method for the amplification of nucleic acids by repeating temperature cycles of denaturation, annealing and extension of a reaction solution containing templates, forward primers, reverse primers, polymerases and dNTPs. Examples include PCR, RT-PCR, real-time PCR, and digital PCR. The above-mentioned PCR in the present invention may be preferably real-time PCR or digital PCR, and most preferably digital PCR.

The above-mentioned "real-time PCR" is a technique for monitoring and analyzing increase of the PCR-amplified products in real time (Levak K J, et al., PCR Methods, Appl., 4(6): 357-62. PCR reaction can be monitored by recording fluorescence emission in each cycle during the exponential phase, during which time the increase of the PCR products is proportional to the initial amount of the target template. The higher the starting copy numbers of the nucleic acid target is, the faster the fluorescence increases and the lower the CT (threshold cycle) value becomes. A pronounced increase in fluorescence above the baseline value measured between 3-15 cycles implies that the accumulated PCR products are being detected. When the amount of PCR-amplified products reaches the amount detectable by fluorescence, the amplification curve begins to occur, and the signal rises exponentially eventually to reach the stagnation state. The larger the initial amount of DNA, the faster the amplification curve appears because the number of cycles with which the amount of amplified product reaches the detectable amount gets smaller. Therefore, when real-time PCR is performed using serially diluted standard samples, amplification curves are obtained arranged in the same intervals and in the order of the initial DNA amounts. When a threshold is set at a suitable point, a CT value is calculated at a point where the threshold and the amplification curve intersect with each other. In real-time PCR, PCR amplification products are detected by fluorescence. Representative detection methods include interchelating methods (SYBR Green I method) and methods using fluorescently labeled probes (TaqMan probe method).

The term "digital PCR" refers to a method in which each nucleic acid molecule present in a sample is divided into a plurality of individual reaction volumes (for example, a chamber or a fraction) and subsequently one or more target sequences are amplified by PCR. Such analytical method for the real-time PCR results display very high signal sensitivity and specificity with small amount of sample as digital PCR captures signals emitted from an individually fractionated chamber or a fraction as opposed to a bulk type where a large amount of signal is emitted.

For digital PCR, see, for example, [Vogelstein and Kinzler, 1999, Proc Natl Acad Sci USA 96: 9236-41; McBride et al., U.S. Patent Application Publication No. 20050252773 (particularly, Example 5)].

In the present invention, a plurality of the internal quality control region may be selected from a single target gene. In this case, PCR may be performed by mixing primers or primers and probes capable of specifically binding to each internal quality control region.

Step (c) is calculating a copy number of the internal quality control region from the result of the PCR;

When the PCR is real-time PCR or digital PCR, the copy number of the target gene may be calculated according to a method of real-time PCR which is commonly performed in the art, and for example, may be calculated according to a method including the following steps:

For example, in case of a general real-time PCR, a standard curve is derived from serially diluted samples of the reference standard material, which is a gene sample with known copy numbers, and the numbers (Cp value or Ct value) of PCR reactions derived from the real-time PCR amplification using those samples are applied on the standard curve to determine the copy numbers in the biological sample.

On the other hand, when the PCR is digital PCR, a large number of droplets are distributed in one well, and a nucleic acid sample, amplification primers, fluorescent probes and DNA amplification polymerases are contained in a droplet. In case of digital PCR, unlike the real-time PCR method, it is an absolute quantitative method in which a single counting method is applied to a target nucleic acid sample without calculating the amount of target nucleic acids using a separate standard curve of a standard material for quantifying target nucleic acids. That is, if target nucleic acids are present in individual droplets distributed in one well, fluorescence signals are amplified by PCR reaction and detected as an independent signal through the fluorescence detection device. Then, the exact copy number of the target nucleic acids can be quantified by measuring the intensity of the detected signals and the number of droplets using the poisson distribution equation.

Step (d) is calculating an internal quality control index (iQC index) according to the following equation:

Internal control quality index=the copy number of the internal quality control region/the copy number of input DNA of the PCR The "copy number of the internal quality control region" means the number of copies of the internal quality control region in the sample calculated in the step (c). The "copy number of input DNA of the PCR" means the number of copies of total nucleic acids or a region to be detected in a sample containing the internal quality control region to amplify, and can be calculated from the nucleic acid value quantified according to the conventional method. For example, in case of human genomic DNA, 3.3 ng of DNA is calculated to have the copy number of input DNA of 1000 copies.

More specifically, the numerical value of the amount of nucleic acids is generally calculated through the conventionally used mole counting method. That is, assuming that 1 bp of the nucleic acid molecule is about 650 Daltons (Da), the number of molecules per gram (mol/g) can be calculated by applying the number of Avogadro species ($6.022 \times 10^{23}$ molecules/mole), the length (bp) and the quantified amount (ng) of the nucleic acids to the following formula.

Equation) number of copies=(amount$\times 6.022 \times 10^{23}$)/ (length$\times 1 \times 10^9 \times 650$) (cels.uri.edu/gsc/cndna.html is referred.)

Step (e) determining that the nucleic acid quality of the sample is appropriate in case where the internal control quality index is equal to or higher than a predetermined threshold, or determining that the nucleic acid quality of the sample is better as the internal control quality index becomes closer to 1.

As described above, the term "nucleic acid quality" of a biological sample in the present invention means preferably whether the nucleic acid region to be detected or analyzed maintains the integrity as an amplifiable state in the biological sample at a certain level.

To this end, in the present invention, the nucleic acid of the "internal quality control region" selected according to the aforementioned criteria is amplified and the number of copies thereof is analyzed to determine whether the same level of copies of the nucleic acid region to be analyzed is contained as the internal quality control region in the specific biological sample.

In the present invention, the "predetermined threshold value" is a value that can be set by a person skilled in the art through a preliminary experiment according to the type of the nucleic acid region to be analyzed and the purpose of analysis, and may be determined by considering the environmental factors which can affect the quality of nucleic acids, such as collection, storage and treatment methods of the biological sample, or may be determined reflecting results of ancillary experiments such as DNA integrity number (DIN) measurement, Sanger sequencing, and the like.

According to one embodiment of the present invention, all 316 samples were classified into four groups according to storage period, DIN value, and iQC copy number. Distributions of DIN and iQC index values were examined for 316 specimens according to the storage period. With the criteria of 6 years of storage, it was observed that the DIN value and the iQC index value of the samples stored more than 6 years were noticeably reduced (FIGS. 5 and 6). DIN values were analyzed for the 57 inconsistent samples among the 169 samples selected from the blocks stored more than 6 years. The DIN values of most of the inconsistent samples were less than 2.5 (FIG. 7). Of the 147 samples with block storage period less than 6 years, 26 samples did not meet the DIN criteria and were included in group 1. To establish the iQC index criteria, we reanalyzed 60 inconsistent samples in group 1, and the iQC index of almost all samples (58/60) were less than 0.5 (FIG. 8).

Based on these results, the sample selection criteria was established as [block storage period≤6 years, DIN>2.5, iQC index≥0.5]. In addition, it was shown that there is a strong correlation between the ddEGFR iQC index and the DIN value (Table 10). In order to verify the clinical usefulness of the iQC index, only the iQC index was used to evaluate the level of agreement, which resulted in the similar agreement as when both the iQC index and the DIN value were applied (Table 11). Thus, these support that the iQC index represents the quality of the nucleic acids.

According to one embodiment of the present invention, the inventors have classified 316 NSCLC FFPE tissues into two groups according to their storage period at room temperature, and examined differences in the internal control quality index of EGFR exon 18-21 between these groups. As a result, it was found that the internal control quality index of the 169 samples with storage period exceeding 6 years was 0.31 on average, while that of the 147 samples with storage period of 2 to 6 years was 1.07. That is, in case of the NSCLC FFPE samples having storage period exceeding 6 years, even if the amplification reaction is carried out using 1000 copies of the input DNA, only 310 copies on average of EGFR exons 18 to 21 can function as amplifiable templates, whereas almost the same copy number of the EGFR exons 18 to 21 as the input DNA can function as amplifiable templates in case of NSCLC FFPE samples with storage period of 2 to 6 years. Therefore, even though the numbers of mutant copies of EGFR exons 18 to 21 detected in the FFPE tissues having storage period of over 6 years and those less than 6 years are the same, it can be problematic planning a patient's treatment strategy based on this.

In case of the above embodiment, the experimenter may set the threshold value as the internal control quality index considering the environmental effect of storage period of the biological sample.

The "threshold value" defined in the present invention is not limited hereto this, but may be a prime number with one significant digit in one decimal place between 0.3 and 0.9, or with two significant digits in any decimal between 0.30 and 0.90, or with three digits with any prime number between 0.300 and 0.900. Preferably, the threshold value is, but not limited hereto, selected from the group consisting of 0.3, 0.4, 0.5, 0.6, 0.7, 0.8, 0.9, 0.30, 0.31, 0.32, 0.33, 0.34, 0.35, 0.36, 0.37, 0.38, 0.39, 0.40, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.78, 0.78, 0.79, 0.80, 0.81, 0.82, 0.83, 0.84, 0.85, 0.86, 0.89, and 0.90. On the other hand, the threshold value can be set by rounding off, rounding up or rounding down to fit the significant digits. Threshold values may also be set equal to or different from each other for two or more target genes or mutations, and may be set equal to or different from each other for two or more internal control quality index.

According to another embodiment of the present invention, the present inventors detected mutations present in EGFR exons 18-21 using nucleic acids extracted from 316 NSCLC FFPE tissues without classifying the samples according to the internal control quality index, and found that there is a very low level of agreement between the commercially available EGFR mutation detection kit (Cobas® EGFR mutation test, Roche, referred to as Cobas EGFR from this on), ddPCR-based EGFR (GenesWell™ ddEGFR mutation test, referred to as ddEGFR from this on) kit and Sanger sequencing results. This means that many of the 316 NSCLC FFPE tissues used in the analysis were damaged in the integrity of the EGFR gene exons 18-21, indicating that reliable results of gene mutation detection were not generated.

According to another embodiment of the present invention, the present inventors selected samples having the internal control quality index of 0.5 or more among the 316 NSCLC FFPE tissues, detected mutations present in EGFR exons 18-21 using the nucleic acids extracted from those samples, and found that there is a very high degree of agreement between the results using the commercially available EGFR mutation detection kit (cobas EGFR) and the ddEGFR test kit. That is, the biological samples exhibiting the threshold value (0.5) of the internal control quality index set under the consideration of the environmental effect of storage period in the above example or even higher can be judged as having the proper nucleic acid quality for the purpose of mutation analysis of EGFR exons 18-21.

As another method for determining the nucleic acid quality of the biological sample, if the internal quality control index calculated in the step (d) is, for example, 1, it means that the copy number of the internal quality control region contained in the biological sample is the same as the copy number of the input DNA, leading to the conclusion that the target nucleic acid region to be analyzed is not damaged in the biological sample, maintaining its integrity as an amplifiable template.

That is, it can be tested whether or not the target gene to be analyzed remains intact in the biological sample prior to performing the gene analysis on the biological sample obtained from the subject for the purpose of clinical studies or companion diagnostics. As a result, it can be judged that the integrity of the target gene is maintained in the biological sample, representing an excellent nucleic acid quality suitable for genetic analysis as the internal control quality index is close to 1.

On the contrary, when the internal control quality index of a specific biological sample is calculated according to the method of the present invention, and for example, if the value is close to 0, it can be considered that most of the target nucleic acid regions included in the biological sample lost their integrity (for example, fragmentation, cross-linking, methylation, oxidative damages, etc.) and exist in a non-amplifiable state, so the quality of the nucleic acids in the biological sample is not good.

The present invention also provides a method in which the primers in the step (b) are the ones having the value [the copy number of the detected internal quality control region/the copy number of the input DNA of the standard material] of 0.90~1.10 when the quantitative PCR is performed on a reference standard material with known copy number of the internal quality control region.

Details related to this will be described later.

The present invention also provides a method for preparing i) primers or ii) a set of primers and a probe, comprising steps of (a) designing i) primers or ii) a set of primers and a probe which are capable of amplifying a nucleic acid fragment of an internal quality control region; (b) performing PCR on a nucleic acid contained in a reference standard substance with the primers or the set of the primers and the probe; (c) calculating a copy number of the internal quality control region from the result of PCR; and (d) selecting primers of which [the copy number of the internal quality control region detected/the copy number of input DNA of the reference standard substance] is 0.90 to 1.10.

Step (a) is designing i) primers or ii) a set of primers and a probe which are capable of amplifying a nucleic acid fragment of the internal quality control region;

In order to amplify a specific region of a gene by PCR, two kinds of synthesized, single-stranded DNAs are required as primers. Primer and/or probe designs and the corresponding overall conditions actually determine the success or failure of the PCR. In the present invention, the primers and/or the probes can be easily prepared using methods known in the art associated with a method of preparing primers and/or probes having sequences complementary to the nucleotide sequences of the internal quality control region.

In the present invention, the terms "primer" and "probe" are as previously described.

When designing primers in the step (a), factors such as, for example, but not limited hereto, 1) length, 2) complementarity between primers, 3) GC content, 4) secondary structure in the primer, 5) Tm value, and 6) concentration etc. are considered. However, it would not be very difficult for a person skilled in the art to design primers specific for the internal quality control region to detect since primer-designing computer programs are commercially available. Here are general factors to consider for designing primers.

(1) Length of a Primer

The length of a primer is suitably 15 to 30 bases, and preferably 17 to 25 bases. Primers of this size may be sufficient to specifically anneal to template DNAs. In case of LA PCR (long and accurate PCR), primers with 30 or more bases can be more effective.

(2) Complementarity Between Primers

It is preferable to design sequences so that two primers do not anneal to each other. In particular, if primers complementary at the 3' end are avoided, risks of degrading amplification efficiency due to primer dimer formation can be reduced.

(3) GC Content

GC content is preferably designed around 50% (40 to 60%, preferably 45 to 55%), preventing partially GC- or AT-rich regions. In addition, the 3' side of the primer should not be AT-rich to ensure that the 3' end of the primer and the template DNA bind stably.

(4) Secondary Structure in the Primer

Self-complementary sequences are avoided to prevent formation of the secondary structures of the primer itself.

(5) Tm

Tm is the median value of the temperature change at which double-stranded DNA becomes single-stranded DNA. This value gets variable depending on the DNA length and the base composition. Higher Tm indicates stronger binding. The stability of the primer-template DNA hybrid is determined by the Tm value, which can be calculated from the following equation based on the experimental data.

$$Tm = 4° C. \times \text{number of}(G+C) + 2° C. \times \text{number of}(A+T)$$

This equation is based on the assumption that the G+C base pair is more stable than the A+T base pair. Primers are designed to have similar Tm values using this equation. The actual annealing temperature should be 2~3° C. lower than the calculated Tm value for primers to bind to the desired position of the target gene accurately.

However, the above equation is appropriate when N (number of bases) is 14 or less. When N>14, it is calculated using the equation $Tm = 64.9 + 41 \times (\text{number of } (G+C) - 16.4)/N$. Alternatively, the adjusted equation of $Tm = 81.5 + 16.6 \times \{\log 10 ([Na^+]+[K^+])\} + 0.41 \times (\% GC) - 675/N$ is used since the Tm value may vary depending on the surrounding salt concentration. However, these calculations are already available as programs and Tm can easily obtained once the base sequence is known.

(6) Other Considerations

Primers are designed avoiding areas of mutations in a target gene to detect (select wild-type area) or of frequent SNP occurrence (5% or more, preferably 1% or more, more preferably 0.5% or more). Designed primer sequences are compared with other sequences on the genome for homology to eliminate possibility of non-specific bindings. It is advisable to exclude primers if any of those considerations apply.

It is also preferable to exclude the case where primer- and/or probe-binding sites are not an "adjacent region" to a target gene (or a mutation in the target gene) or a mutation site. The "adjacent region" is as previously described.

Considering general factors as previously described, primers of various sequences which specifically bind to a target gene to be detected; or sets of primers and probes can be designed and optimal primers; or primers and probes can be selected by the following steps.

Step (b) performing PCR on a nucleic acid contained in a reference standard substance with the primers or the set of the primers and the probe; step (c) is calculating a copy number of the internal quality control region from the result of PCR.

Details are as previously described regarding the primers of various sequences designed in the step (a); or the method to perform PCR using sets of primers and probes and to use the PCR results to perform PCR as steps to calculate copy numbers of the internal quality control region, and the method to calculated the copy number of the internal quality control region.

In the present invention, the reference standard material is the material having a predetermined number of copies of a target gene. For example, major mutations of EGFR are artificially introduced into a cell line having wild-type EGFR gene using a genome editing (gene scissoring) technique (CRISPR/Cas9). Subsequently produced cells containing EGFR mutations are mixed with wild-type cells at a specific ratio, fixed with paraffin to produce FFPE blocks which will function as a standard material with a constant mutation frequency. Standard materials may be commercially available from companies like Horizon such as those shown in Table 3.

TABLE 3

| Gene | Annino Acid Change | Chromosome | Exon | Transcript ID(GRCh37) | COSMIC ID | dbSNP ID |
|---|---|---|---|---|---|---|
| ABL1 | T315I | chr9 | Exon6133748247_133748424 | ENST00000318560 | COSM12560 | rs121913459 |
| ABL2 | P986fs | chr1 | Exon12179078576_179068462 | ENST00000344730 | COSM2095020 | N/A |
| AKT1 | E17K | chr14 | Exon4105246553_105246425 | ENST00000349310 | COSM33765 | rs121434592 |
| ALK | F1174L | chr2 | Exon2329443689_29443560 | ENST00000389048 | COSM28055 | N/A |
| ALK | P1543S | chr2 | Exon229415640_29416788 | ENST00000389048 | COSM2941442 | N/A |
| APC | R2714C | chr5 | Exon5112173250_112181936 | ENST00000257430 | COSM2991126 | N/A |
| ARID1A | P1562fs | chr1 | Intron | ENST00000324856 | N/A | N/A |
| BRAF | V600E | chr7 | Exon7140453075_140453193 | ENST00000288602 | COSM476 | rs113488022 |
| BRAF | V600G | chr7 | Exon7140453075_140453193 | ENST00000288602 | COSM6137 | rs113488022 |
| BRAF | V600K | chr7 | Exon7140453075_140453193 | ENST00000288602 | COSM473 | rs121913227 |
| BRAF | V600M | chr7 | Exon7140453075_140453193 | ENST00000288602 | COSM1130 | rs121913378 |
| BRAF | V600R | chr7 | Exon7140453075_140453193 | ENST00000288602 | COSM474 | rs121913227 |
| BRCA2 | A1689fs | chr13 | Downstream | ENST00000380152 | N/A | N/A |
| CCND2 | N/A | chr12 | N/A | ENST00000261254 | N/A | rs3217808 |
| CDH1 | N/A | chr16 | 3'UTR | ENST00000261769 | N/A | N/A |
| CDX2 | V306fs | chr13 | Exon328537506_28536274 | ENST00000381020 | N/A | N/A |
| CTNNB1 | S33Y | chr3 | Exon341266017_41266202 | ENST00000349354 | COSM5673 | rs121913400 |
| CTNNB1 | S45del | chr3 | Intron | ENST00000426215 | COSM12628 | N/A |
| EGFR | G719S | chr7 | Exon1855241614_55241736 | ENST00000275493 | COSM6252 | rs28929495 |
| EGFR | L858R | chr7 | Exon2155191719_55191874 | ENST00000275493 | COSM6224 | rs121434568 |
| EGFR | L861Q | chr7 | Exon2155191719_55191874 | ENST00000275493 | COSM6213 | rs121913444 |
| EGFR | T790M | chr7 | Exon2055248986_55249171 | ENST00000275493 | COSM6240 | rs121434569 |
| EGFR | ΔE746-A750 | chr7 | Exon2055248986_55249171 | ENST00000275493 | COSM6223 | rs121913421 |
| EGFR | S768I | chr7 | Exon1955174772_55174870 | ENST00000275493 | COSM6241 | rsl 21913465 |
| EGFR | G719A | chr7 | Exon2055248986_55249171 | ENST00000275493 | COSM6239 | rs121913428 |
| EGFR | S492R | chr7 | Exon1855241614_55241736 | ENST00000275493 | COSM236670 | N/A |
| EGFR | V769_D770insASV | chr7 | Exon1225398208_25398329 | ENST00000275493 | COSM12376 | N/A |
| EP300 | K291fs | chr22 | Intron | ENST00000263253 | N/A | N/A |
| FANCA | E345fs | chr16 | Downstream | ENST00000389301 | N/A | N/A |
| FBXW7 | G667fs | chr4 | Intron | ENST00000263981 | N/A | N/A |
| FGFR1 | P124L | chr8 | Exon838285439_38285611 | ENST00000335922 | N/A | N/A |
| FGFR2 | S252W | chr10 | Exon7123279683_123279493 | ENST00000358487 | COSM36903 | rs79184941 |
| FLT3 | D835Y | chr13 | Exon2028592726_28592604 | ENST00000241453 | COSM783 | rs121913488 |

TABLE 3-continued

| Gene | Annino Acid Change | Chromosome | Exon | Transcript ID(GRCh37) | COSMIC ID | dbSNP ID |
|---|---|---|---|---|---|---|
| FLT3 | S985fs | chr13 | Intron | ENST00000241453 | N/A | N/A |
| FLT3 | V197A | chr13 | Exon1328626682_28626811 | ENST00000241453 | COSM2070177 | N/A |
| FLT3 | ΔI836 | chr10 | Exon2028592726_28592604 | ENST00000241453 | COSM797 | rs121913490 |
| GNA11 | Q209L | chr19 | Exon53118922_3119051 | ENST00000078429 | COSM52969 | N/A |
| GNAQ | Q209L | chr9 | Exon580409524_80409653 | ENST00000286548 | COSM28757 | rs121913492 |
| GNAS | R201C | ch20 | Exon857484405_57484478 | ENST00000371085 | COSM27887 | rs11554273 |
| IDH1 | R132C | chr2 | Exon4209113384_209113093 | ENST00000345146 | COSM28747 | rs121913499 |
| IDH1 | R132H | chr2 | Exon4209113384_209113093 | ENST00000345146 | COSM28746 | rs121913500 |
| IDH1 | S261L | chr2 | Exon2209106718_209106869 | ENST00000345146 | COSM1669701 | N/A |
| IDH2 | R140Q | chr15 | Exon490631979_90631819 | ENST00000330062 | COSM41590 | rs121913502 |
| IDH2 | R172K | chr15 | Exon490631979_90631819 | ENST00000330062 | COSM33733 | rs121913503 |
| JAK2 | V617F | chr9 | Exon145073698_5073785 | ENST00000381652 | COSM12600 | rs77375493 |
| KIT | D816V | chr4 | Exon1755599236_55599358 | ENST00000288135 | COSM1314 | rs121913507 |
| KRAS | A146T | chr12 | Exon425378707_25378548 | ENST00000256078 | COSM19404 | rs121913527 |
| KRAS | A59T | chr12 | Exon325380346_25380168 | ENST00000311936 | COSM546 | rs121913528 |
| KRAS | G12A | chr12 | Exon22539869_2539748 | ENST00000256078 | COSM522 | rs121913529 |

Step (d) selecting primers of which [the copy number of the internal quality control region detected/the copy number of input DNA of the reference standard substance] is 0.90 to 1.10;

The primers and probes prepared according to the primer and probe preparation method of the present invention are intended to be used for judging the integrity of target genes contained in a biological sample. Therefore, it is important to select primers highly sensitive to the internal quality control region selected from the base sequences of the target gene, and to this end, the selection method of the step (d) may be applied.

The copy number of input DNA of the reference standard material can be quantified by measurements and the figures calculated in step (C) can be used for the copy number of the internal quality control region.

Primers of various base sequences; or sets of primers and probes designed in the step (a) may exhibit different sensitivities and specificities depending on many factors. As the ratio of the copy number of the internal quality control region detected using the copy number of input DNA of the reference standard material and primers of specific base sequences is closer to 1, it can be understood that the primers; or the sets of primers and probes for the internal quality control region are highly sensitive.

Therefore, selection criteria is whether the copy number of the detected internal quality control region corresponds to the copy number of input DNA of the reference standard material, in other words, whether the copy number of the internal quality control region is detected as much as the copy number of the nucleic acids of the reference standard material used in the experiments. More specifically, in the present invention, primers can be selected in which the value of [the copy number of internal quality control region detected/the copy number of input DNA of the reference standard material] is 0.90 to 1.10, preferably 0.91 to 1.09, 0.92 to 1.08, 0.93 to 1.07, 0.94 to 1.06, 0.95 to 1.05, 0.96 to 1.04, 0.97 to 1.03, and most preferably 0.98 to 1.03. Further, when the amplification value (amplitude) of the control region is low, it is difficult to carry out ensuing experiments. Therefore, it is preferable to select primers or a set of primers and probes having the highest amplification value among others satisfying the above range.

Thus, in the present invention, primers capable of amplifying the internal quality control region (for both primers alone and the primers included in the set of primers and probes) are the ones satisfying the criteria of [detected copy number of the internal quality control region/copy number of input DNA of the reference standard material] between 0.90~1.10 as well as the "adjacent region" in the primer design.

Since primers; or a set of primers and probes prepared according to the above methods are very sensitive to the internal quality control region in the base sequences of the target nucleic acid, they can be very useful in confirming whether the integrity of target nucleic acids in a biological sample is maintained as a amplifiable form.

The present invention also provides a method for calculating a % mutation index of a target gene in a biological sample, the method comprising the steps of: (a) extracting a nucleic acid from a biological sample obtained from a subject; (b) performing a first PCR on the extracted nucleic acid with i) primers or ii) a set of primers and a probe which are capable of amplifying an internal quality control region; (c) calculating a copy number of the internal quality control region from the result of the first PCR; (d) performing a second PCR on the extracted nucleic acid with iii) primers or iv) a set of primers and a probe which are capable of amplifying a target gene or mutation site; (e) calculating the copy number of the target gene or the mutation site from the result of the second PCR; and (f) calculating a % mutation index according to the following equation:

% Mutation index=the copy number of the target gene or mutation site/the copy number of the internal quality control region×100.

The field of mutation analysis of genes is rapidly growing with emphasis on the importance of various clinical analysis and diagnostics such as diagnosis of human genetic diseases, pharmacogenetics, drug development and microbiology. In the field of genetics, a mutation means a change in the base sequences including insertion/deletion in the frame of a specific gene, base substitution, and single nucleotide polymorphism (SNP) as well as translocation and inversion. Most widely used method for analyzing gene mutations is the PCR-based method. Compared to other mutation analysis methods, PCR is advantageous because it is fast, highly sensitive and specific, low cost, and easy to automate.

On the other hand, traditional methods based on PCR to detect gene mutations generally derive the mutation frequency by calculating the ratio of mutations to input DNA. However, as described above, nucleic acids in a biological sample can be modified in various ways while going through a series of treatments such as collection, storage and pre-treatment. If the nucleic acids containing mutations to be detected are not conserved in a PCR-amplifiable form due to those modifications, the calculated mutation frequency may show significant difference from the actual mutation frequency present in the nucleic acids in a biological sample.

Accordingly, the present inventors applied the concept of the internal quality control index (iQC index) which evaluates the nucleic acid quality of a biological sample to the mutation frequency calculation method, and devised a new concept of % mutation index (MI) representing the ratio of the mutation copy number to the copy number of actually amplifiable templates, thereby providing a method to standardize a frequency of a specific mutation contained in the nucleic acids of a biological sample.

In the present invention, the % mutation index can be calculated according to the following equation:

% Mutation index=[copy number of the target gene or mutation site/copy number of the internal quality control region×100](unit:%)

In the above method of the present invention, the "target gene" and the "internal quality control region" are as described above.

The fact that the internal quality control region can be PCR-amplifiable means that the nucleic acid region containing the areas of mutations to detect (including both wild-type and mutant) can be determined as an amplifiable template. The fact that the internal quality control region satisfying the above criteria cannot be amplified by PCR means that numerous types of modification has happened to the nucleic acid region containing the area of mutations to detect (including both wild-type and mutant), making it unable to be amplified.

Therefore, the value of the "copy number of the internal quality control region" in the above equation can be regarded as the same as the number of amplifiable copies of the nucleic acid region containing the area of mutations to detect (including both wild-type and mutant). Based on this, the detected mutant copy numbers can be standardized.

In reference to the above equation, the % mutation index of the present invention represents the mutation rate as compared with the actually amplifiable template, unlike the conventional mutation rate based on input DNA, which is very meaningful since it can provide objective values closest to the actual mutation rate of the nucleic acids of a biological sample to be analyzed.

For example, if the number of copies of input DNA to perform quantitative PCR is 1000 and the number of copies of the mutation site detected by the quantitative PCR is 200, the mutation rate calculated according to the conventional method equals 20%. However, if only 500 copies among 1000 input DNA copies were amplified due to various types of nucleic acid modifications (that is, if the copy number of the internal quality control region was 500), the 20% mutation rate cannot be an objective figure. On the other hand, according to the % mutation index suggested in the present invention, the value of [200 copies of the mutant gene/500 copies of the amplifiable templates×100]=40%, and the value of 40% indicates the objective and standardized value of a mutation frequency present in the nucleic acids in a biological sample to be analyzed.

In the present invention, the methods used in each step of the method to determine the nucleic acid quality can be applied in the same manner to each step included in the % mutation index calculating method.

Meanwhile, in the present invention, the steps (b) to (e) can be performed in one step as a multiplex PCR reaction by mixing primers capable of amplifying the internal quality control region; or sets of primers and probes capable of amplifying the target gene or mutation site; or sets of primers and probes. In this case, it is preferable to design each primer; or each set of primers and probes so that each primer; or each set of primers and probes does not mutually interfere and can independently amplify the complementary sequences with high specificity and sensitivity.

Moreover, it is also possible to calculate the copy number of the internal quality control region by performing the first PCR of steps (b) and (c), and to calculate the copy number of target genes or mutant sites by performing the second PCR of steps (d) and (e) simultaneously, sequentially, or by changing the order, all of which are included in the scope of the present invention.

The present invention also presents a method in which the target gene is epidermal growth factor receptor (EGFR) exon 18 to 21, and the mutation is one or more selected from the group of inframe deletion of bases, inframe insertion of bases and base substitution in EGFR exon 18 to 21.

EGFR is recognized as a target of lung cancer treatment. Development of EGFR tyrosine kinase inhibitors (EGFR-TKI) is a representative example of cancer treatment targeting EGFR. Currently, gefitinib (Iressa) and erlotinib (Tarceva) have been developed as tyrosine kinase inhibitors useful for the treatment of lung cancer, particularly non-small cell lung cancer. However, when clinically applied, many patients are resistant or irresponsive to those EGFR tyrosine kinase inhibitors from the very beginning. Further, only 10-15% of the advanced lung cancer patients respond to the EGFR kinase inhibitors. Previous studies on this have found that the presence of somatic mutations in the kinase domain of EGFR significantly increases the sensitivity of EGFR kinase inhibitor drugs. The EGFR mutations are mainly observed in females, Asians, non-smokers, and adenocarcinoma lung cancer patients, and the presence of such mutations is associated with drug reactivity and patient prognosis. EGFR mutations are mainly observed in exon 18 to exon 21, among which the most common mutant forms are the inframe deletion in exon 19 or the L858R point mutation in exon 21, and in particular, the T790M point mutation has been reported to contribute significantly to drug resistance to EGFR kinase inhibitor drugs. It was reported that NSCLC patients having EGFR mutations were significantly more responsive to EGFR kinase inhibitor drugs than those without EGFR mutations, leading to a significant increase in survival. Likewise, since the presence of an EGFR mutations act as a strong predictor of drug sensitivity to EGFR kinase inhibitors such as zetifinib or erlotinib, it is important to detect EGFR mutations in an objective and reliable manner according to the methods of the present invention for the optimal therapeutic approaches.

Preferably, the mutations appearing in EGFR exons 18-21 of the present invention may be one or more of the mutations listed in Table 4 below.

TABLE 4

| No. | Target exon | COSMIC No. | Target mutant A.a | Target mutant site |
|---|---|---|---|---|
| 1 | Exon19 | 6223 | p.E746_A750del | c.2235_2249 del 15 |
| 2 |  | 13551 | p.E746_T751 > I | c.2235_2252 > AAT |
| 3 |  | 12728 | p.E746_T751del | c.2236_2253 del 18 |
| 4 |  | 12678 | p.E746_T751 > A | c.2237_2251 del 15 |

TABLE 4-continued

| No. | Target exon | COSMIC No. | Target mutant A.a | Target mutant site |
|---|---|---|---|---|
| 5 | | 12367 | p.E746_S752 > A | c.2237_2254 del 18 |
| 6 | | 12384 | p.E746_S752 > V | c.2237_2255 > T |
| 7 | | 6225 | p.E746_A750del | c.2236_2250 del 15 |
| 8 | | 6220 | p.E746_S752 > D | c.2238_2255 del 18 |
| 9 | | 13550 | p.E746_A750 > IP | c.2235_2248 > AATTC |
| 10 | | 12403 | p.L747_S752 > Q | c.2239_2256 > CAA |
| 11 | | 12422 | p.L747_A750 > P | c.2238_2248 > GC |
| 12 | | 12419 | p.L747_T751 > Q | c.2238_2252 > GCA |
| 13 | | 6218 | p.L747_E749del | c.2239_2247 del 9 |
| 14 | | 12382 | p.L747_A750 > P | c.2239_2248 TTAAGAGAAG > C |
| 15 | | 6210 | p.L747_T751 > S | c.2240_2251 del 12 |
| 16 | | 12383 | p.L747_T751 > P | c.2239_2251 > C |
| 17 | | 13552 | p.E746_T751 > IP | c.2235_2251 > AATTC |
| 18 | | 6254 | p.L747_T751del | c.2239_2253 del 15 |
| 19 | | 6255 | p.L747_S752del | c.2239_2256 del 18 |
| 20 | | 12387 | p.L747_P753 > Q | c.2239_2258 > CA |
| 21 | | 12370 | p.L747_P753 > S | c.2240_2257 del 18 |
| 22 | | 12416 | p.E746_T751 > VA | c.2237_2253 > TTGCT |
| 23 | | — | — | c.2239_2257 > GT |
| 24 | | 26038 | p.K745_E749del | c.2233_2247del15 |
| 25 | | 13556 | p.S752_I759del | c.2253_2276del24 |
| 26 | | 12386 | p.E746_T751 > V | c.2237_2252 > T |
| 27 | | 12385 | p.E746_S752 > I | c.2235_2255 > AAT |
| 28 | | 18427 | p.E746_P753 > VS | c.2237_2257 > TCT |
| 29 | | 12369 | p.L747_T751del | c.2240_2254 del 15 |
| 30 | | 23571 | p.L747_T751delLREAT | c.2238_2252 del 15 |
| 31 | Exon20 | 6240 | p.T790M | c.2369C > T |
| 32 | Exon21 | 6224 | p.L858R | c.2573T > G |
| 33 | | 12429 | p.L858R | c.2573_2574TG > GT |
| 34 | Exon18 | 6239 | p.G719A | c.2156G > C |
| 35 | | 6252 | p.G719S | c.2155G > A |
| 36 | | 6253 | p.G719C | c.2155G > T |
| 37 | Exon20 | 6493937 | p.C797S | c.2389T > A |
| 38 | | 5945664 | p.C797S | c.2390G > C |
| 39 | | — | p.C797S | c.2388, 89 CT > AA |
| 40 | Exon20 | 6241 | p.S768I | c.2303G > T |
| 41 | Exon20 | 12376 | p.V769_D770insASV | c.2307_2308 insGCCAGCGTG |
| 42 | | 12377 | p.H773_V774insH | c.2319_2320 insCAC |
| 43 | | 12378 | p.D770_N771insG | c.2310_2311 insGGT |
| 44 | | 13428 | p.D770_N771insSVD | c.2311_2312insGCGTGGACA |
| 45 | | 13558 | p.V769_D770insASV | c.2309_2310AC > CCAGCGTGGAT |
| 46 | Exon21 | 6213 | p.L861Q | c.2582T > A |

The present invention also provides a method for standardizing a mutational frequency of a target gene or mutation site in a biological sample, the method comprising the steps of:

(a) measuring the mutational frequency of a target gene or mutation site in a biological sample; and (b) calculating a standardizing mutation frequency by dividing the measured mutation frequency by an internal quality control index of the sample.

In the present invention, the "mutation frequency" (or mutation rate) is a conventionally referred mutation rate meaning a value of [copy number of the mutation site detected by PCR/copy number of the input DNA], which is different from the mutation index (MI) of the present invention. In addition, the "internal control quality index" is as described above.

The "copy number of the mutation site" in the above [number of copies of the mutation site detected by PCR/number of copies of the input DNA] can be calculated by performing PCR using primers capable of amplifying the mutation site; or a set of primers or probes as described above.

According to the method for standardization of the mutation rate of the present invention, it is possible to objectively compare the expression ratios of mutations between biological samples, thereby providing reliable information in the field of clinical research and companion diagnostics.

Advantageous Effect

According to the methods of the present invention, it is possible to objectively evaluate the nucleic acid quality in a biological sample used for gene analysis and to provide objective results about the occurrence rate of genetic mutations, therefore it is effective in providing reliable information in the fields of clinical research and companion diagnostics.

BRIEF DESCRIPTION OF DRAWINGS/FIGURES

Figure 3:
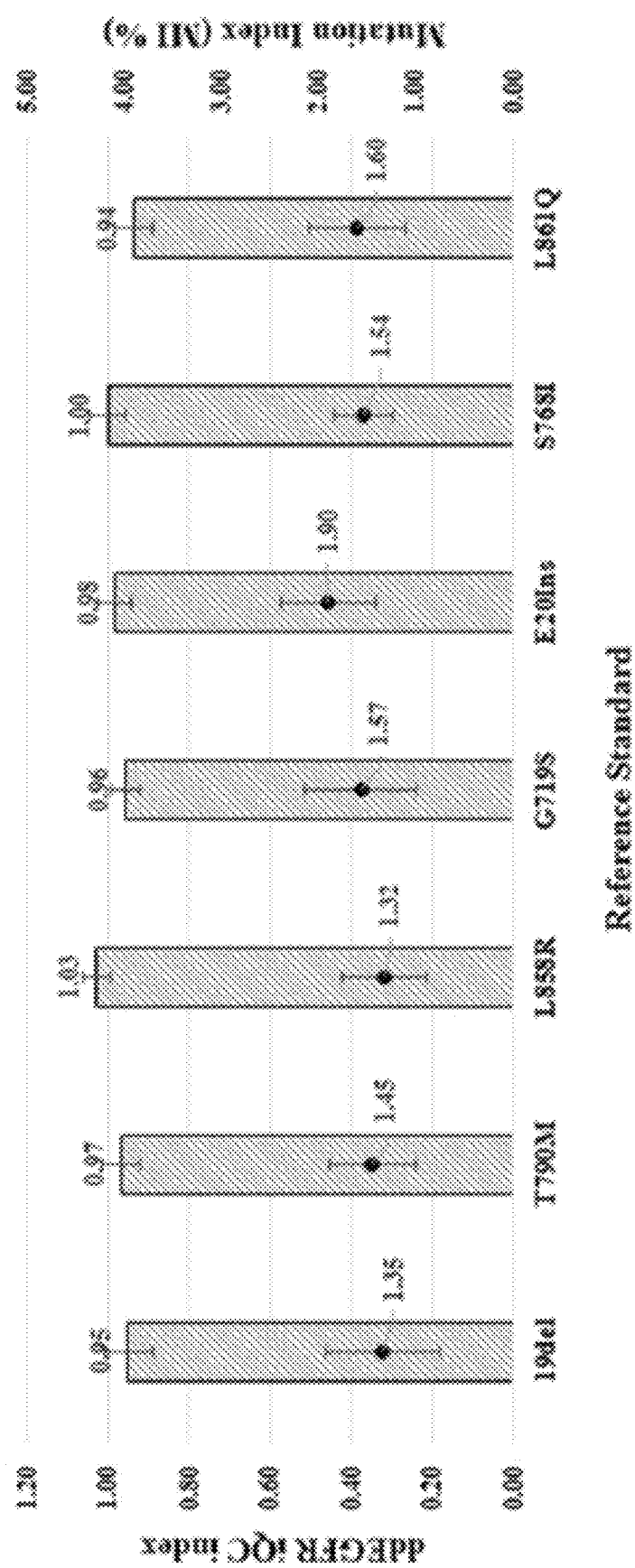

FIG. 3 shows the results to validate the internal quality control of ddEGFR experiments. Each FFPE reference standard DNA extract for EGFR mutations was mixed with a fixed amount wild-type gDNA (3.3 ng, 1,000GE), targeting the mutation level of 1.5% which was validated for the use in the ddEGFR test. Numbers are represented as mean±SD of nine experiments.

Figure 4:
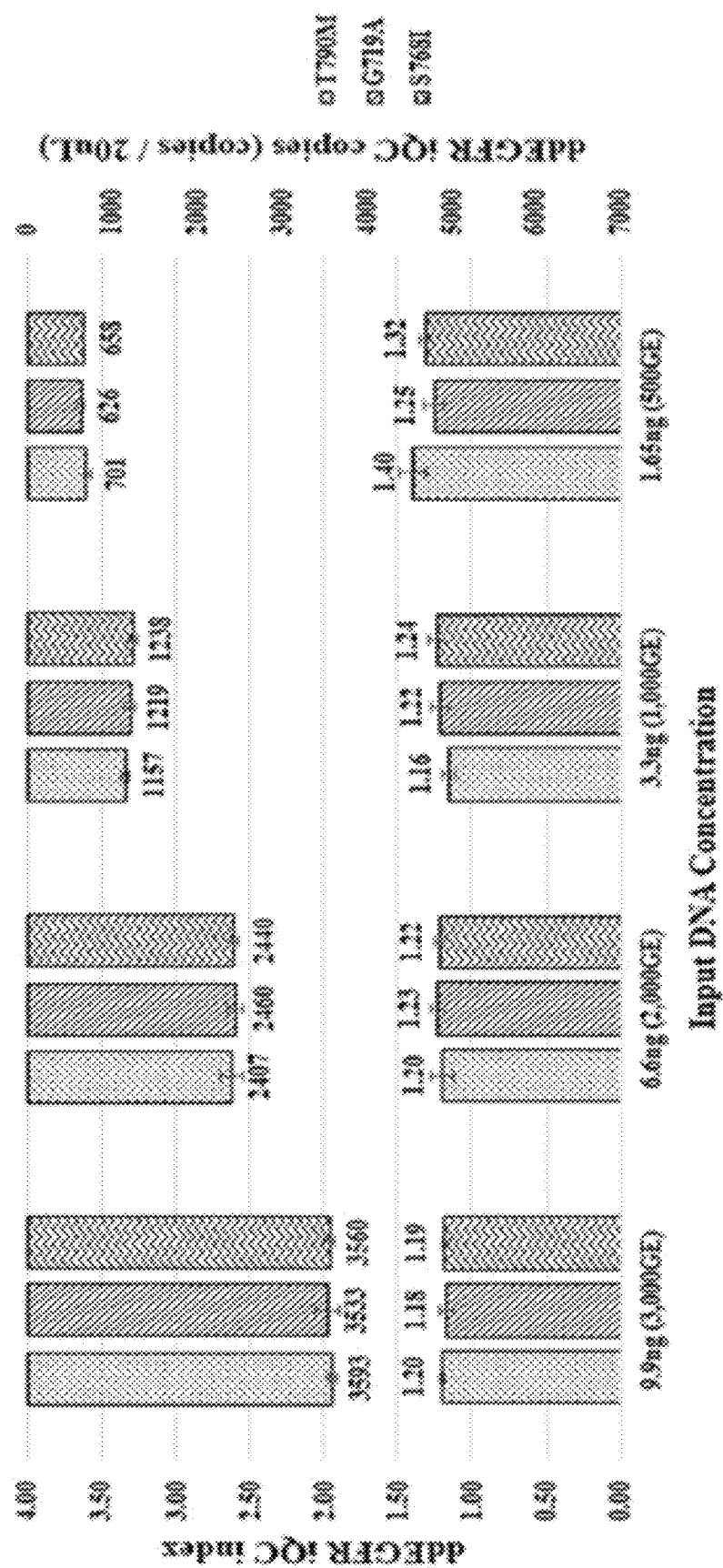

FIG. 4 shows the results to validate the internal quality control of ddEGFR experiments. Each FFPE reference standard DNA extract was used to prepare four consecutive serial dilutions and ddEGFR experiments were carried out. Error bars represent SD. Numbers are represented as mean±SD of three experiments.

Figure 5:
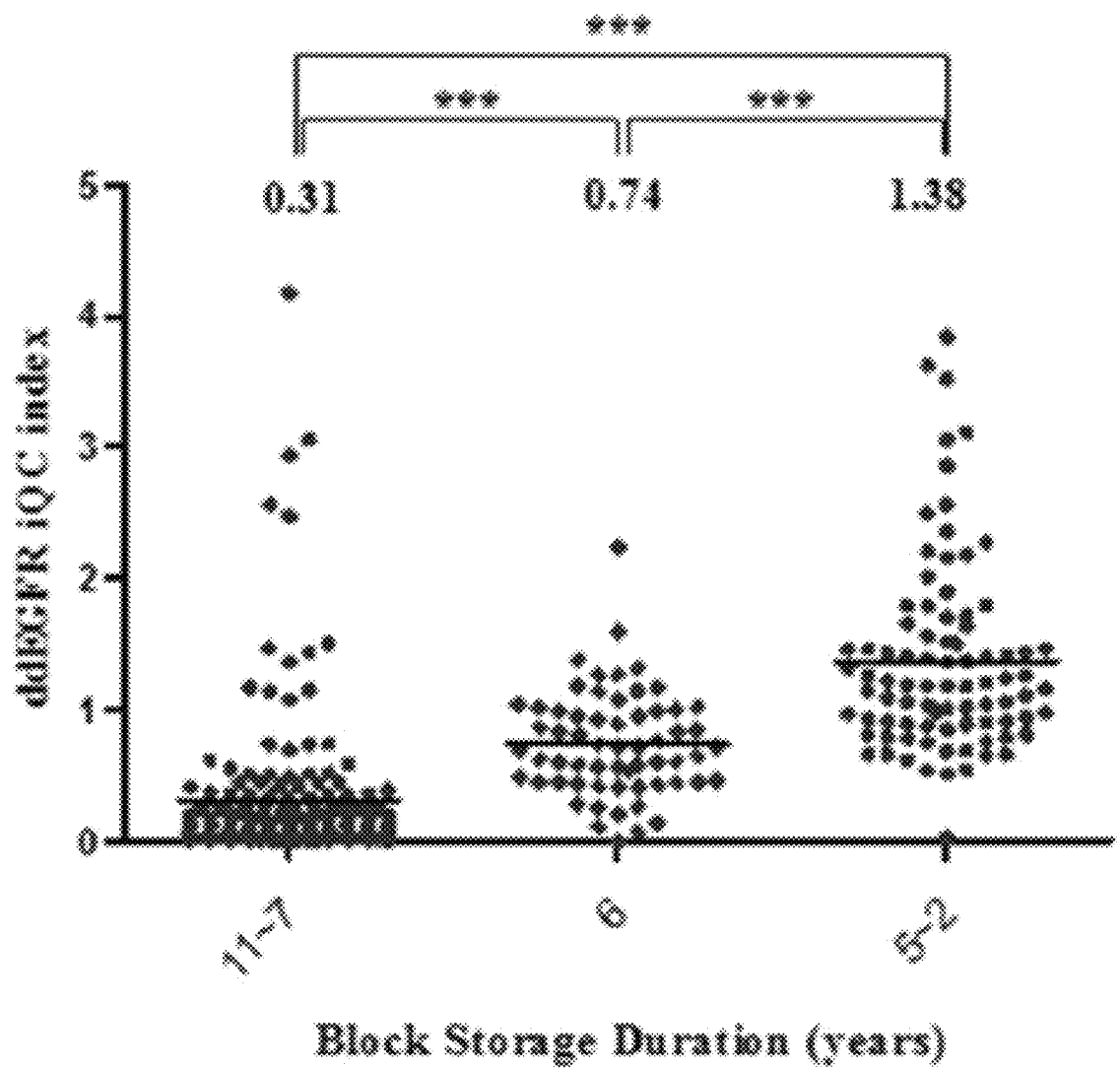

FIG. 5 shows the results from the experiments to establish sample selection criteria in a diagram illustrating distributions of the ddEGFR iQC index according to the sample storage period (black solid line represents the average of the result values).

Figure 6:
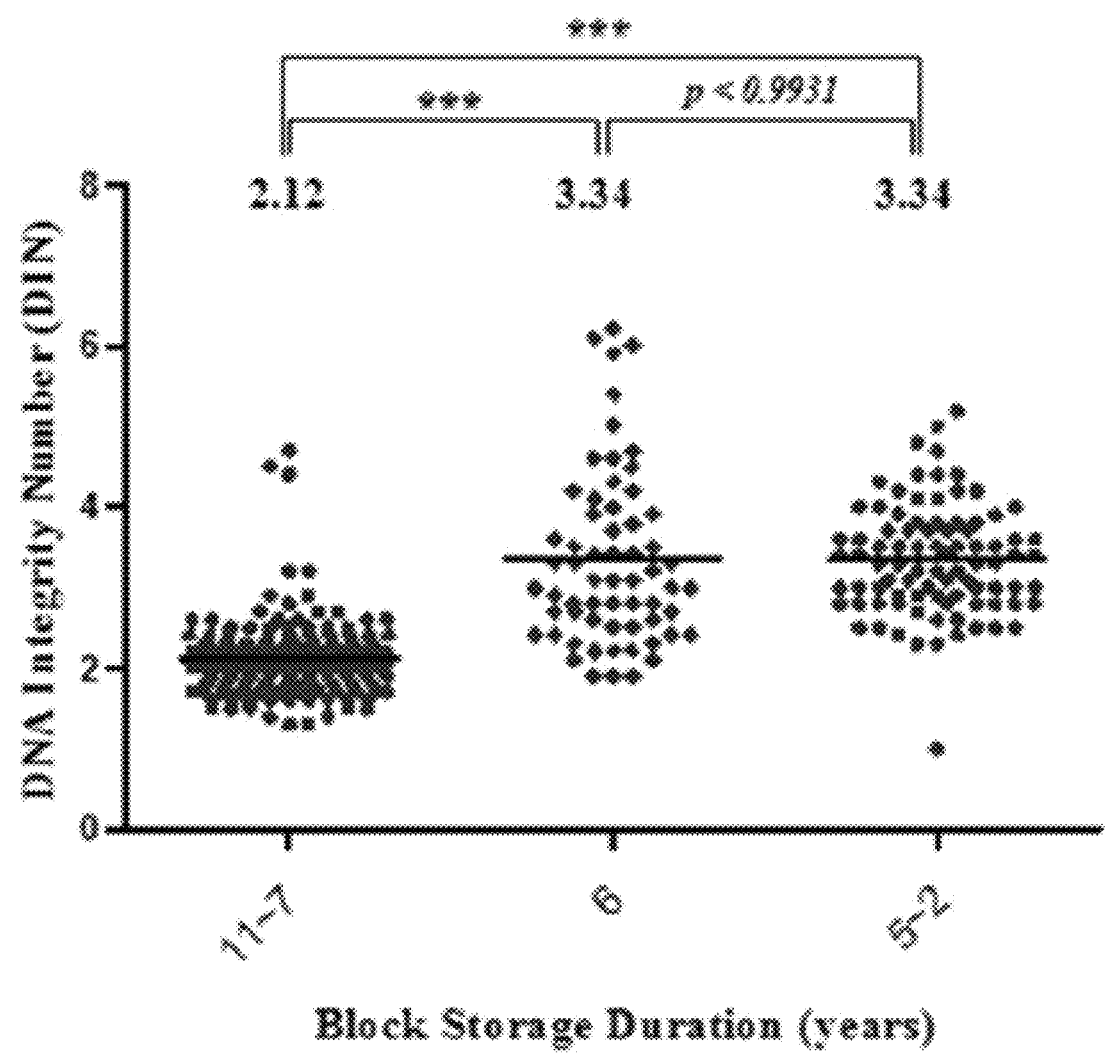

FIG. 6 shows the results from the experiments to establish sample selection criteria in a diagram illustrating distributions of the DIN values according to the sample storage period of a sample (black solid line represents the average of the result values).

Figure 7:
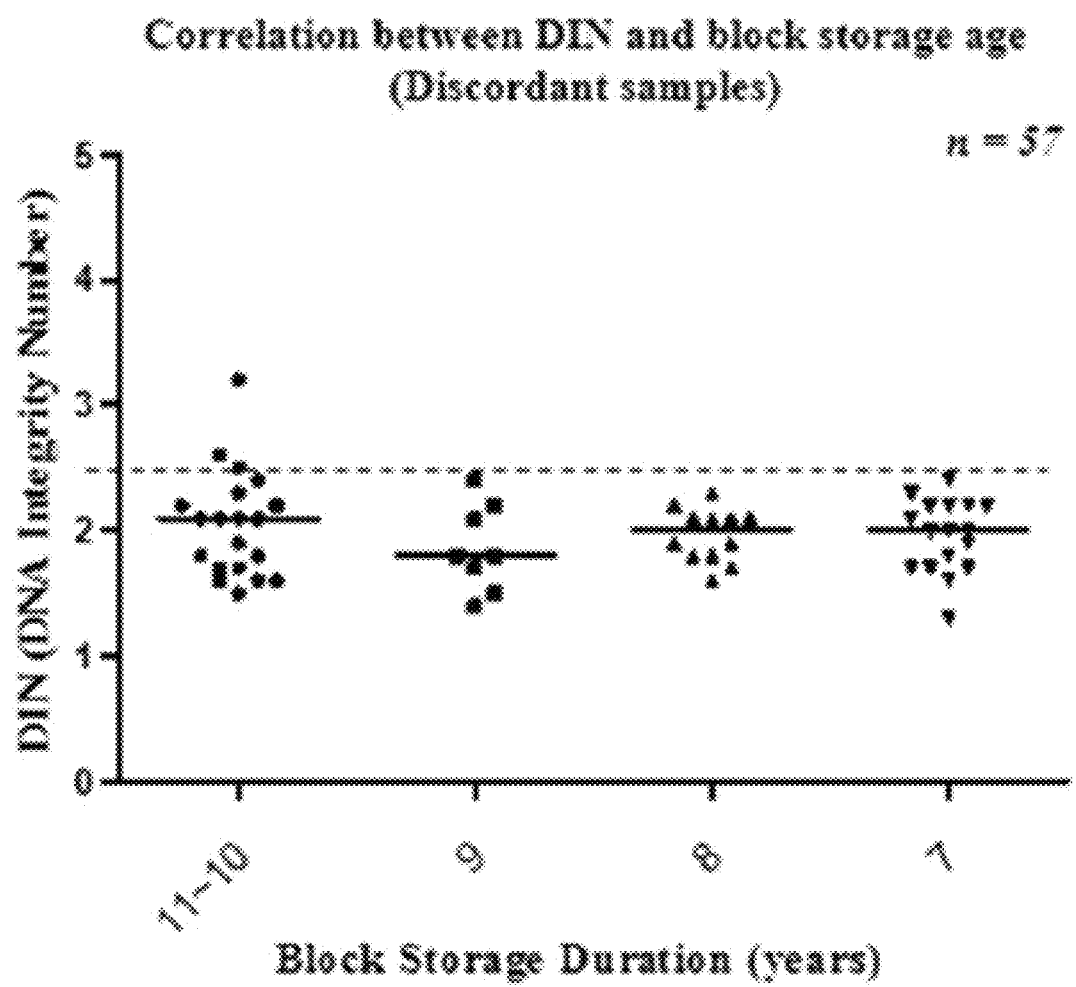

FIG. 7 shows the results from the experiments to establish sample selection criteria in a diagram illustrating the correlation between the storage period of the samples with inconsistent results and the DIN value (black solid line represents the average of the result values).

Figure 8:
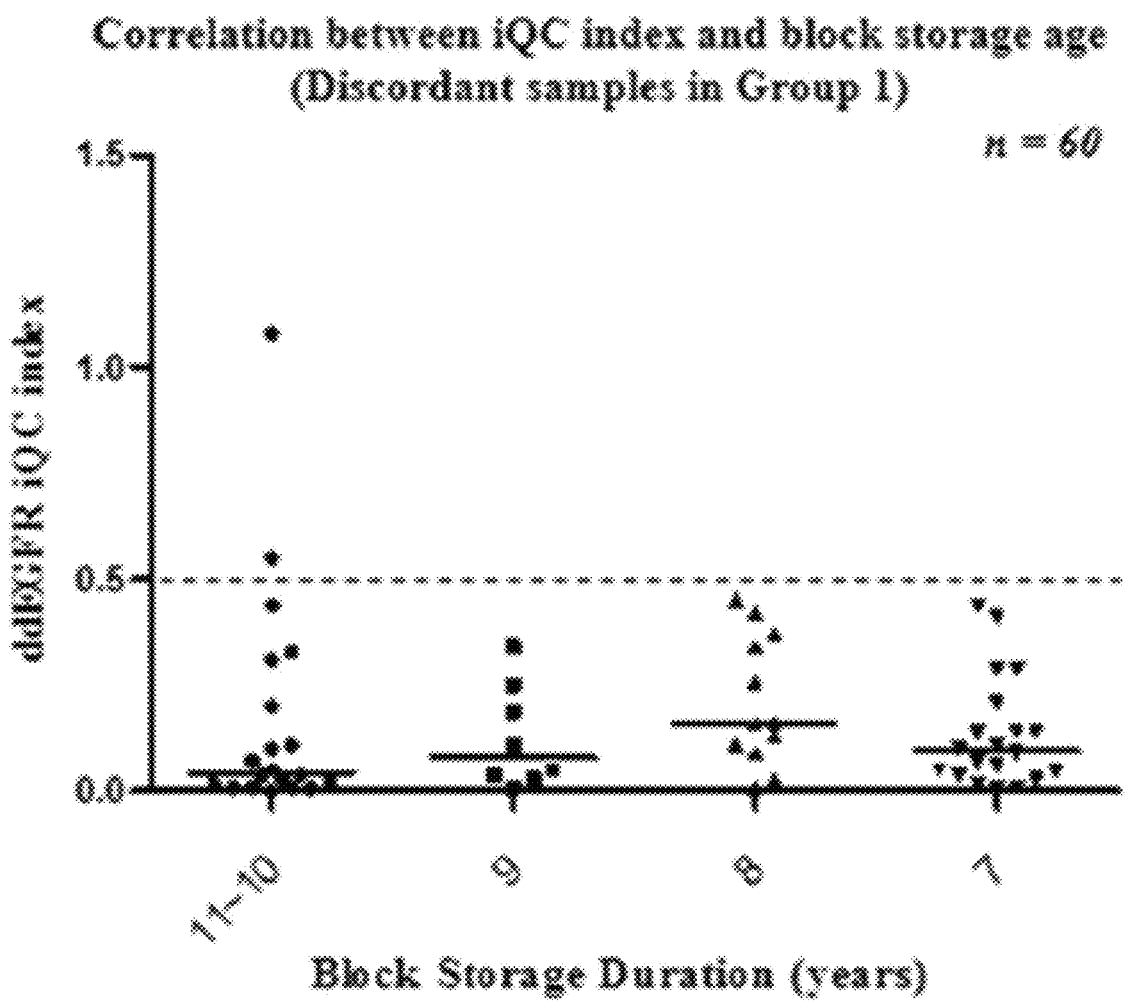

FIG. 8 shows the results from the experiments to establish sample selection criteria in a diagram illustrating the correlation between the storage period of the samples with inconsistent results and the iQC index (black solid line represents the average of the result values).

Figure 9:
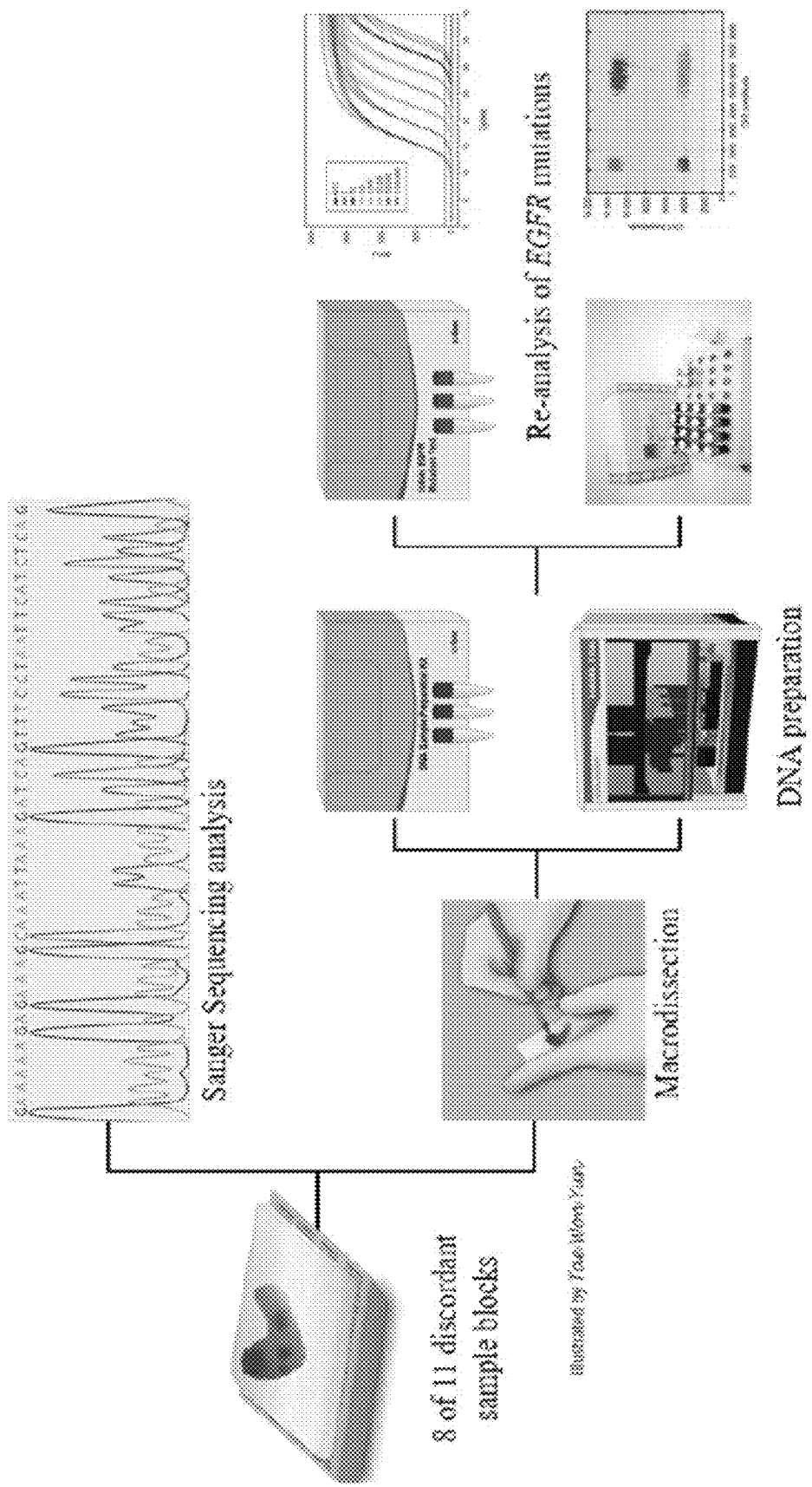

FIG. 9 is a diagram showing the process of reanalyzing the inconsistent samples.

FIG. 10 is a table showing the results of reanalyzing eight samples among eleven samples which exhibited inconsistent results in group 3 (MD: mutation detected, MND: mutation not detected, N/A: FFPE blocks not available). Eight of the eleven samples were verified by sequencing.

FIG. 11 shows diagrams displaying distributions of the iQC index (A) and the DIN (B) according to the block storage period.

Figure 12:
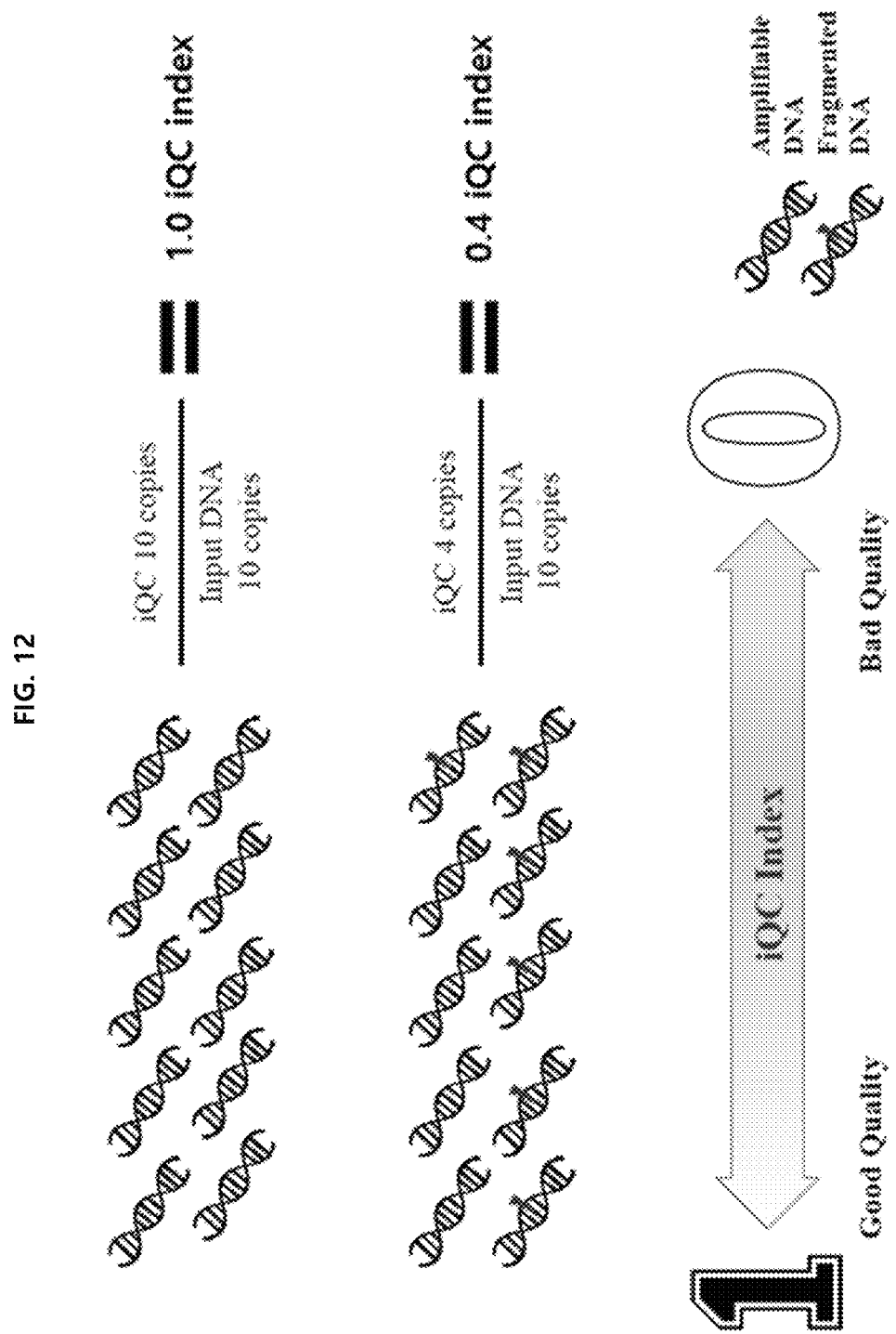

FIG. 12 shows diagrams summarizing and explaining the concept of the iQC index according to the present invention.

Figure 13:
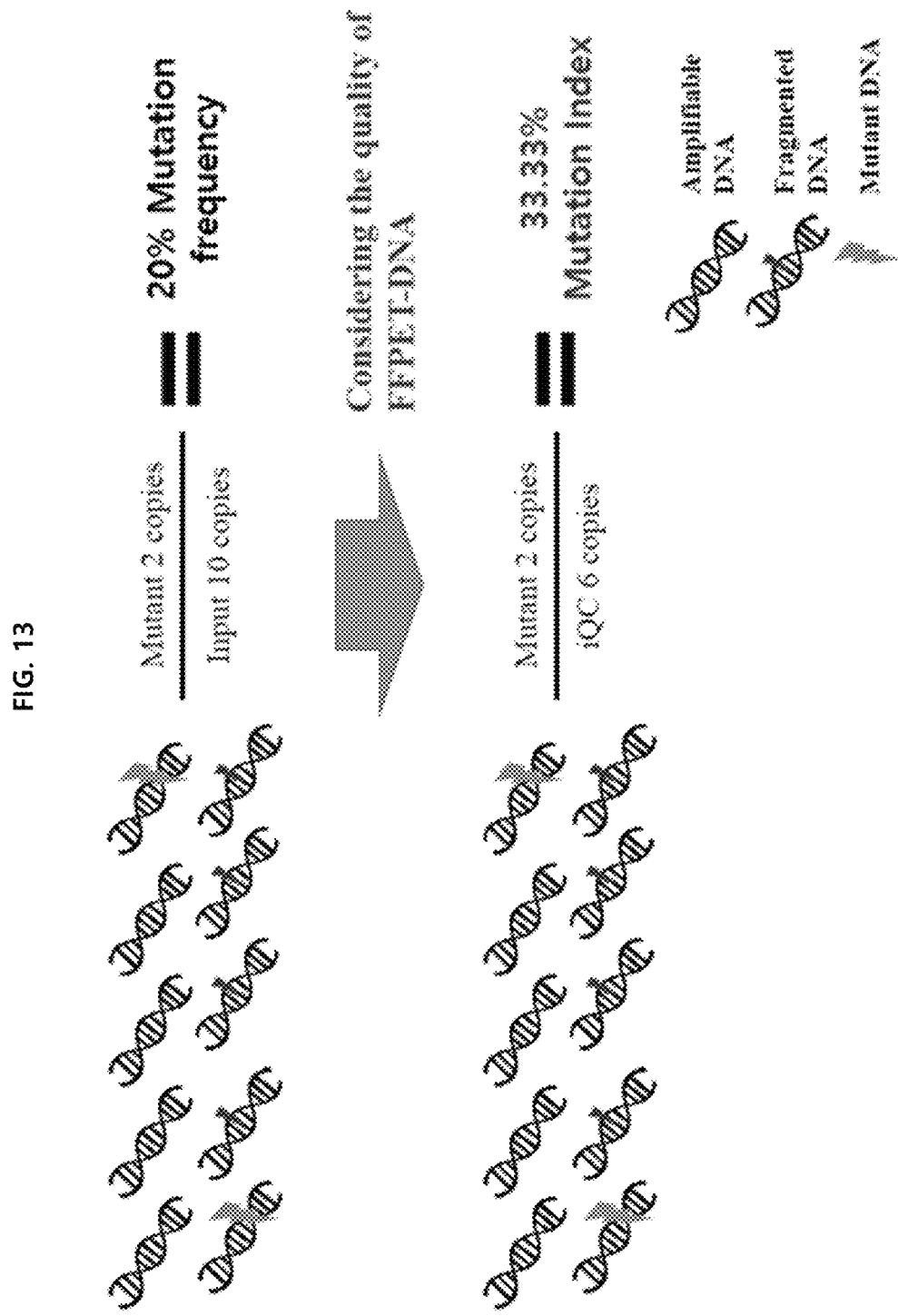

FIG. 13 shows diagrams summarizing and explaining the concept of the mutation index (MI) in accordance with the present invention.

MODE FOR CARRYING OUT INVENTION

Hereinafter, the present invention will be described in detail.

However, the following examples are only illustrative of the present invention, and the present invention is not limited hereto the following examples.

<Experimental Methods>

1. Research Design

Figure 1:
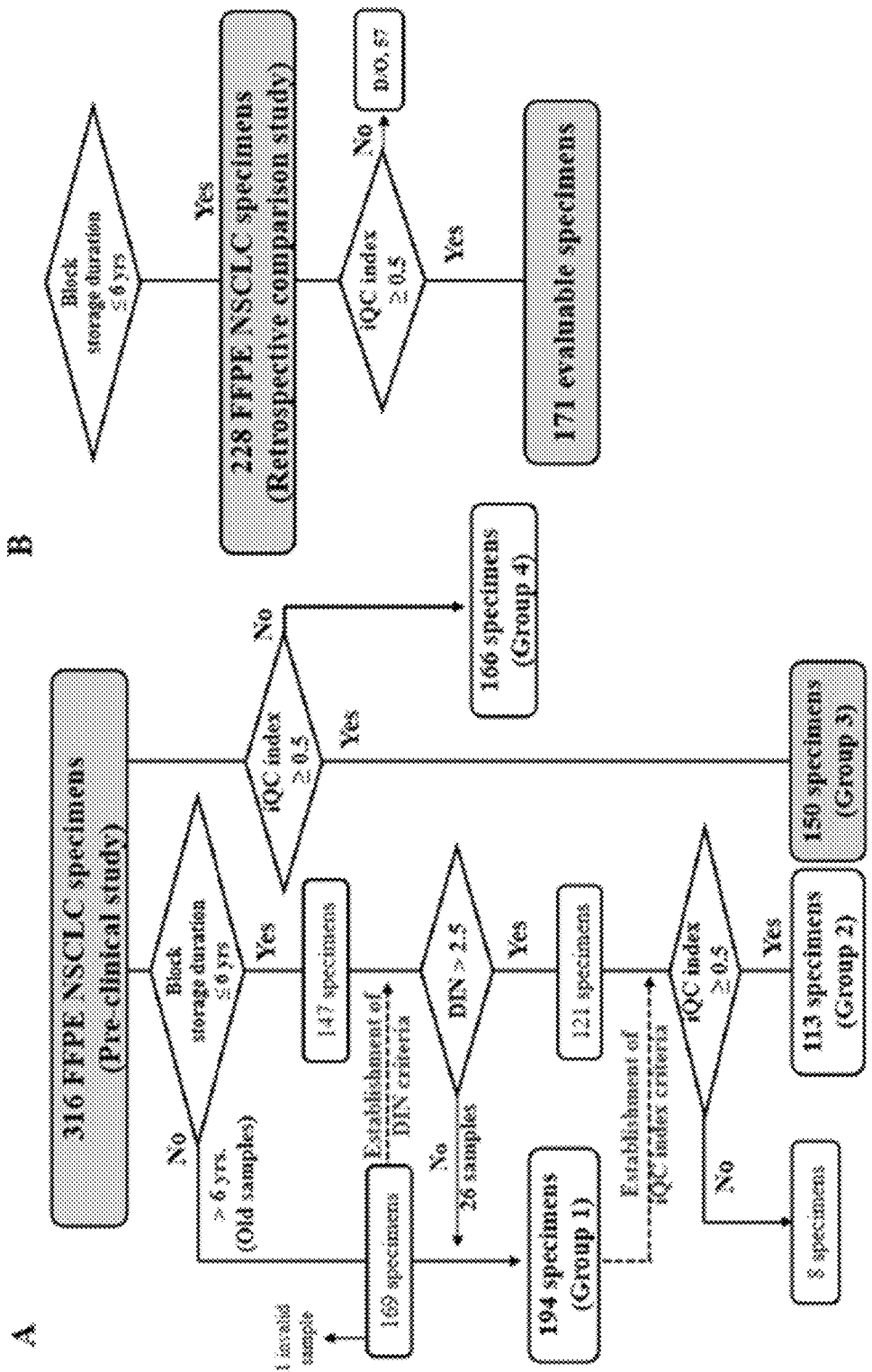
FIG. 1 shows schematic diagrams displaying the criteria for selecting a biological sample (FFPET) in accordance with the present invention and the number of samples thus selected (A: preclinical trial work flow to establish sample selection criteria, B: workflow of the selection criteria for the retrospective comparative test, D/O: Drop Out).

To establish the sample criteria, a total of 316 samples from non-small cell lung cancer (NSCLC) patients were tested for EGFR mutations. Post-hoc analyses of these preclinical data were performed for all the results from the ddEGFR and cobas EGFR tests. Based on the established sample criteria, an independent retrospective comparative study was conducted to assess the agreement between the ddEGFR and cobas EGFR assays; For this, 228 FFPET-DNA samples from NSCLC patients were analyzed using two tests. Two EGFR mutation tests were performed in a double-blind fashion in independent experiments (Abion Inc., Seoul, Korea). A schematic diagram of the research workflow is shown in FIG. 1.

The main research objective was 1) to establish the minimum standard for determining the DNA quality of a biological sample suitable for genetic analysis using PCR, and 2) to verify the technique of the present invention by comparing the results of the ddEGFR and the cobas EGFR test.

2. FFPET Collection, DNA Extraction and Determination of the Amount and Quality of DNA The FFPET (formalin-fixed, paraffin-embedded tissue) blocks of resected or biopsied specimens of NSCLC patients (n=316) collected from 2005 to 2014 were obtained from Samsung Hospital (n=200, SMC, Seoul), Asan Medical Center (n=66, AMC, Seoul) and Severance Hospital (n=50, Seoul). The study was approved by the SMC and Seoul National University Institutional Review Board (IRB) (Study ID: SMC-2014-05-084-002). For the retrospective comparative study, a total of 228 archived FFPET blocks of NSCLC patients collected between 2010 and 2016 were obtained from the SMC pathology departments. The study was approved by the SMC's and Korea Food and Drug Administration's IRB (Study ID: SMC-2016-07-104-002).

Patient information was anonymized before analysis. From each FFPET, 10 μm sections were sliced and DNA extraction was performed. The H&E stained sections containing tumor lesions marked by pathologist (SWC) were scanned and analyzed using the Panoramic Viewer Software v.1.15.4 (3DHISTECH, Budapest, Hungary) to calculate cancer/normal (C/N) ratios. DNA extraction from FFPET was performed using an automated tissue preparation system (TPS, Siemens Healthcare, Erlangen, Germany) containing VERSANT® tissue preparation reagents. The total nucleic acids were eluted with 100 μL of elution buffer. DNA concentrations were measured for all the samples using Qubit™ 3.0 fluorescence meter (ThermoFisher Scientific, MA, USA). The DNA integrity number (DIN) reflecting the DNA fragmentation level of genomic DNA (gDNA) was analyzed using the 2200 TapeStation system using Genomic DNA Screen Tape (Agilent Technologies, CA, USA).

3. Validation of the Internal Quality Control (iQC) of the ddEGFR Test

The ddEGFR test (Gencurix Inc., Seoul, Korea) was designed as a highly sensitive ddPCR-based diagnostic test which detects 45 mutations in exons 18-21 region of EGFR gene using four reactions. Amplified fragments containing Fluorophores FAM™ or HEX™ are represented by droplets and can be used to calculate the concentrations (copies/20 µL) according to the Poisson distribution.

Details of the EGFR mutations detected as as result of the analysis are shown in Table 5 below.

TABLE 5

| Exon | Mutations detected | Mutation report cell | LoB copies/MI(%)* | LoD MI(%)† |
|---|---|---|---|---|
| 18 | G719A, C719C, G719S | G719X | 5.6/0.22 | 0.77 |
| 19 | 30 deletions | 19del | 3.0/0.09 | 0.83 |
| 20 | S768I | S768I | 1.5/0.05 | 0.83 |
|  | T790M | T790M | 6.8/0.34 | 0.78 |
|  | C797S§ | C797S | 1.6/0.03 | 0.75 |
|  | 5 Insertions | E20Ins | 1.6/0.06 | 0.62 |
| 21 | L858R | L858R | 1.6/0.03 | 0.71 |
|  | L861Q | L861Q | 1.4/0.05 | 0.74 |

Non-clinical studies followed the guidelines approved by the Clinical and Laboratory Standards Institute (CLSI) and Korea-MFDS. To verify the internal quality control of the ddEGFR, the FFPE reference standard DNA extract containing EGFR mutations (HDx™ Reference Standard, Horizon Discovery, Cambridge, UK) was mixed with a fixed amount of wild-type gDNA (3.3 ng, 1,000 GE, Promega, Fitchburg, WI, USA) and each sample with a target mutation index (MI) of 1.5%.

In addition, four consecutive serial dilutions (9.9 ng, 6.6 ng, 3.3 ng and 1.65 ng) of each sample were prepared and analyzed using the ddEGFR assay. The iQC copies and the target MI of each sample were confirmed based on the input DNA concentration and the target MI (1.5%) (in the present invention, the iQC copy number means the copy number of the EGFR gene detected in a particular FFPET sample from the PCR analysis using primers of this experiment.)

3. Biomarker Analysis ddEGFR assay was performed in a 20 µL volume containing 3.3 ng (1,000 GE) of template DNA/reaction in a Droplet Digital™ PCR (ddPCR) system (Bio-Rad, Hercules, CA, USA). ddPCR analysis was performed according to the previously reported method. Detection thresholds were set manually based on the results from the negative control wells containing wild-type gDNA (Promega) and control wells without template DNA. PCR amplification for the cobas EGFR assay (Roche Molecular Systems Inc., Branchburg, NJ, USA) was performed on a Cobas® z480 analyzer. Cobas EGFR assay requires 150 ng of total input DNA. Those two types of mutation testing methods were analyzed in a double-blind fashion and the results were compared after analysis.

For mutagenic screening of EGFR exons 18, 19, 20 and 21 by 2× bidirectional Sanger sequencing, target genes were amplified by PCR and the amplified samples were analyzed using a validated protocol in the independent laboratory (Macrogen, Seoul, Korea). Sanger sequencing results were cross-checked and analyzed by a pathologist (Y. L. C.).

4. Correlation Between Methods and Statistical Analysis

Agreement analysis for all the methods was based on the mutation report call in the above Table 5. Statistical analysis was performed using GraphPad Prism™ (GraphPad Software Inc., San Diego, USA) and the R 1.6.12 package 'psych' (CRAN.R-project.org/package=psych). We calculated the 95% confidence interval (CI) corresponding to Positive Percent Agreement (PPA), Negative Percent Agreement (NPA) and Overall Percentage Agreement (OPA) for agreement analysis.

<Experimental Results>

Validation of the Internal Quality Control (iQC) in the ddEGFR

Since a ddPCR-based test is inherently very sensitive and can cause false-positive results due to the nature of FFPET, cut-off of the ddEGFR test was determined based on a false-positive analysis using normal formalin-fixed, paraffin-embedded FFPET.

Mutation calls were confirmed based on true-positive mutation values which were higher than the limit of blank (LoB), the limit of detection (LoD) and the mutation index (MI) established from the analytical performance study (Table 5). MI is a value indicating the ratio of the mutation to the copy number of the internal quality control (iQC) calculated according to the following formula (1).

$$\text{Mutation index}(\%) = \frac{\text{Mutant copies}}{\text{iQC copies}} \times 100 \quad (1)$$

In the ddEGFR test, the iQC copy number can be converted into the input DNA concentration using the FFPE reference standard. Thus it can be understood that the iQC index (2) is an index indicating amplifiable DNA. Since the number of iQC copies was analyzed using the input DNA of 3.3 ng (1,000 genome equivalents [GE]) per reaction well, the iQC index was calculated according to the following formula (2).

$$\text{iQC index} = \frac{\text{iQC copies}}{\text{Input DNA copies}} \quad (2)$$

Figure 2:
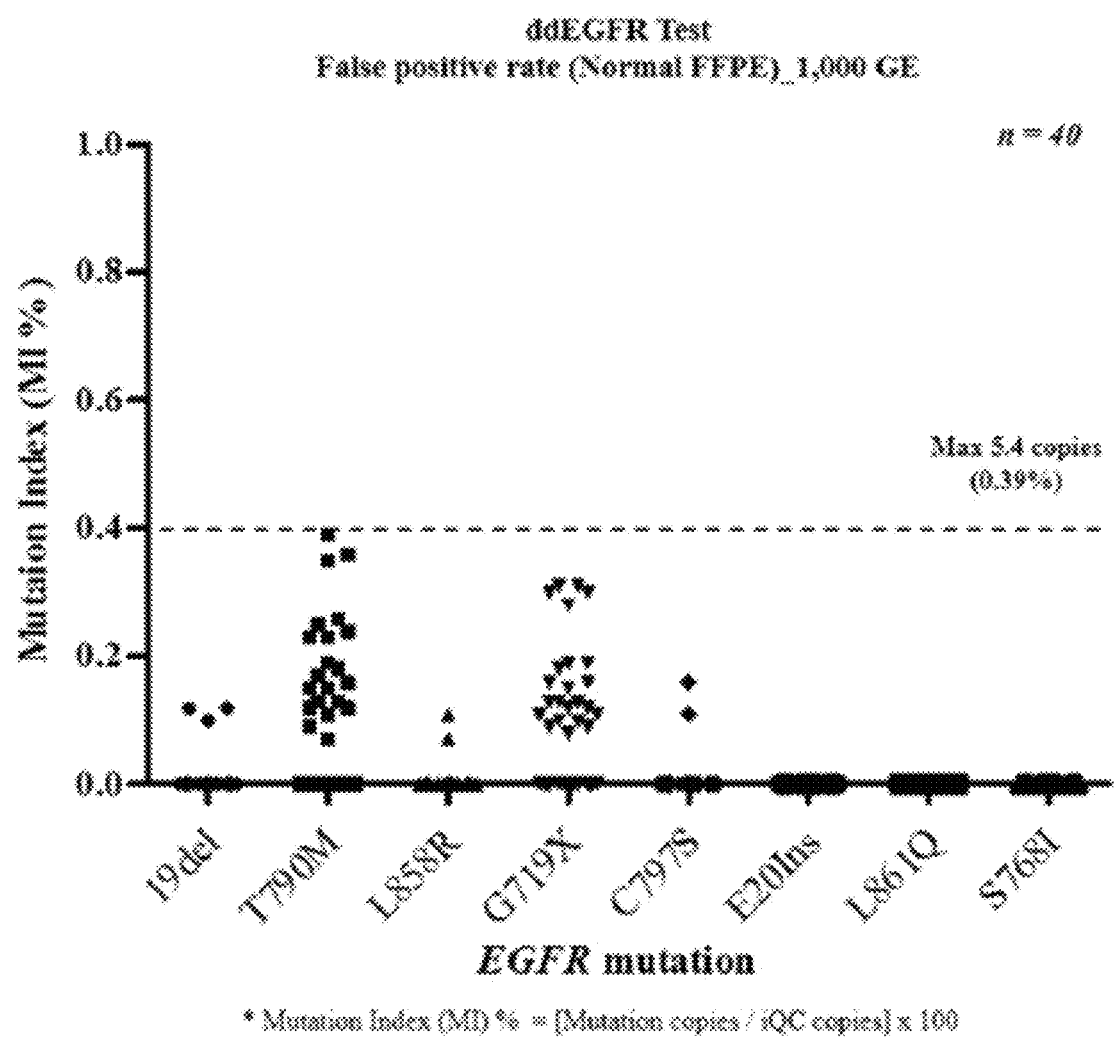
FIG. 2 is a diagram showing the results from the experiments to determine the appropriate cut-off based on false-positive analysis using normal FFPE blocks.

Forty wild-type FFPET samples were used to determine the false-positive rate of mutation callings for eight targets. The maximum number of copies was 5.4 per reaction and the false-positive rate was less than 0.5% of MI (FIG. 2). The present inventors evaluated iQC using the reference standard. The FFPET-DNA reference standard containing EGFR mutations was mixed with a fixed amount of wild-type gDNA (3.3 ng, 1,000 GE) targeting a mutation level of 1.5%. Expected iQC index and MI were calculated from the measured amount of the input DNA, and the measured MI (%) and iQC index were almost identical to the predicted values (iQC index=1, MI=1.5%). Also, iQC was verified with four concentrations of serially diluted reference standard FFPET-DNA, which confirmed that the measured values were in agreement with the predicted values (FIG. 4), and the iQC copy number represents the amount of the input DNA.

2. Comparison of ddEGFR and Cobas EGFR Performed without Sample Selection Criteria EGFR mutations in 316 non-small cell lung cancer (NSCLC) FFPET samples were analyzed using ddEGFR and cobas assay. Both methods yielded valid results, with the exception of one among all samples. Surprisingly, ddEGFR and cobas EGFR test results showed low consistency (positive percent agreement (PPA)=94.04%, negative percent agreement (NPA)=63.41%, overall percent agreement (OPA)=78.10%, kappa coefficient value (κ)=0.6650) (Table 6 and Table 7).

TABLE 6

| All Samples (n = 316) | | cobas EGFR Test | | |
|---|---|---|---|---|
| | | MB | MND | Total |
| ddEGFR Test | MD | 139 | 62* | 201 |
| | MND | 9 | 104 | 113 |
| | Total | 148 | 166 | 314 |
| PPA (95% C.I.) | | 94.04% (88.99-97.24%) | | |
| NPA (95% C.I.) | | 63.41% (55.55-70.79%) | | |
| OPA (95% C.I.) | | 78.10% (73.12-82.54%) | | |

TABLE 6-continued

| All Samples (n = 316) | cobas EGFR Test | | |
|---|---|---|---|
| | MB | MND | Total |
| PPV (95% C.I.) | 70.30% (63.48-76.51%) | | |
| NPV (95% C.I.) | 92.04% (85.42-96.29%) | | |

1 Sample: Invalid
*3 samples: cobas EGFR, 19del; ddEGFR, 19delT790M
1 sample: cobas EGFR, 19del; ddEGFR, 19delL858R
1 sample: cobas EGFR, E20Ins; ddEGFR, E20Ins T790M
1 sample: cobas EGFR, S768I; ddEGFR, S768IL858R

TABLE 7

| All Samples (n = 316) | | cobas EGFR Test | | | | | | | |
|---|---|---|---|---|---|---|---|---|---|
| | | G719X | 19del | T790M | E20Ins | S768I | L858R | G719X, T790M | G719X, S768I |
| ddEGFR Test | G719X | 1 | | | | | | | |
| | 19del | | 85 | | | | | | |
| | T790M | | | 0 | | | | | |
| | E20Ins | | | | 0 | | | | |
| | S768I | | | | | 0 | | | |
| | L858R | | 1† | | | | 48 | | |
| | G719X, T790M | | | | | | | 0 | |
| | G719X, S768I | | | | | | | | 3 |
| | 19del, T790M | | 3 | | | | | | |
| | 19del, L858R | | 1 | | | | | | |
| | T790M L858R | | | | | | | | |
| | T790M, E20Ins | | | | 1 | | | | |
| | S768I, L858R | | | | | 1 | | | |
| | MND | | | | | | | | |
| | Total | 1 | 99 | 0 | 1 | 1 | 48 | 0 | 3 |

| All Samples (n = 316) | | cobas EGFR Test | | | | | | |
|---|---|---|---|---|---|---|---|---|
| | | 19del, T790M | 19del, L858R | T790M L858R | T790M, E20Ins | S768I, L858R | MND | Total |
| ddEGFR Test | G719X | | | | | | | 2 |
| | 19del | | | | | | | 89 |
| | T790M | | | | | | | 0 |
| | E20Ins | | | | | | | 2 |
| | S768I | | | | | | | 0 |
| | L858R | | | | | | | 96 |
| | G719X, T790M | | | | | | | 1 |
| | G719X, S768I | | | | | | | 3 |
| | 19del, T790M | 0 | | | | | | 3 |
| | 19del, L858R | | 0 | | | | | 1 |
| | T790M L858R | | | 0 | | | | 1 |
| | T790M, E20Ins | | | | 0 | | | 1 |
| | S768I, L858R | | | | | 2 | | 3 |
| | MND | | | | | | 104 | 113 |
| | Total | 0 | 0 | 0 | 0 | 2 | 160 | 315 |

†1 sample was excluded from the analysis
1 sample: Invalid
κ coefficient = 0.6650 (35% C.I. 59.98-73.03%)

Cobas EGFR test showed very low consistency with the Sanger sequencing results of 299 samples as well (PPA=59.30%, NPA=75.00%, OPA=65.63%, κ=0.4526) (Table 8 and Table 9).

TABLE 8

| W/O Criteria(n = 299) | | Sanger sequencing | | |
|---|---|---|---|---|
| | | MD | MND | Total |
| cobas EGFR test | MD | 102 | 29* | 131 |
| | MND | 70† | 87 | 157 |
| | Total | 172 | 116 | 285 |

TABLE 8-continued

| W/O Criteria(n = 299) | Sanger sequencing | | |
|---|---|---|---|
| | MD | MND | Total |
| PPA (95% CI) | 59.30% (61.56-66.72%) | | |
| NPA (95% CI) | 75.00% (66.11-82.57%) | | |
| OPA (95% CI) | 65.63% (59.83-71.10%) | | |
| PPV (95% CI) | 77.86% (69.78-84.65%) | | |
| NPV (95% CI) | 55.41% (47.28-63.34%) | | |

*1 sample: Sanger, L858R; cobas EGFR, L858R, S768I
†4 samples: Sanger, 19del, L858R; cobas EGFR, 19del
1 sample: Sanger, 19del, L858R; cobas EGFR, L858R

TABLE 9

| W/O Criteria (n = 299) | | Sanger Sequencing | | | | | | | |
|---|---|---|---|---|---|---|---|---|---|
| | | G719X | 19del | T790M | E20Ins | S768I | L858R | 19del, G719X | 19del, T790M |
| ddEGFR Test | G719X | 0 | | | | | | | |
| | 19del | | 62 | | | | | 8§ | |
| | T790M | | | 0 | | | | | |
| | E20Ins | | | | 0 | | | | |
| | S768I | | | | | 0 | | | |
| | L858R | | 2§ | | | | 40 | | |
| | 19del, G719X | | | | | | | 0 | |
| | 19del, T790M | | | | | | | | 0 |
| | 19del, L858R | | | | | | | | |
| | G719X, T790M | | | | | | | | |
| | G719X, S768I | | 1§ | | | | | | |
| | T790M, L858R | | | | | | | | |
| | S768I, L858R | | | | | | 1 | | |
| | MND | | 24 | | | | 27 | 1 | |
| | Total | 0 | 89 | 0 | 0 | 0 | 76 | 1 | 0 |

| W/O Criteria (n = 299) | | Sanger Sequencing | | | | | | |
|---|---|---|---|---|---|---|---|---|
| | | 19del, L858R | G719X, T790M | G719X, S768I | T790M, L858R | S768I, L858R | MND | Total |
| ddEGFR Test | G719X | | | | | | 1 | 1 |
| | 19del | 4 | | | | | 18 | 92 |
| | T790M | | | | | | | 0 |
| | E20Ins | | | | | | 1 | 1 |
| | S768I | | | | | | | 0 |
| | L858R | 1 | | | | | 5 | 48 |
| | 19del, G719X | | | | | | | 0 |
| | 19del, T790M | | | | | | | 0 |
| | 19del, L858R | 0 | | | | | | 0 |
| | G719X, T790M | | 0 | | | | | 0 |
| | G719X, S768I | | | 0 | | | 2 | 3 |
| | T790M, L858R | | | | 0 | | | 0 |
| | S768I, L858R | | | | | 0 | 1 | 2 |
| | MND | 13 | | | | | 87 | 152 |
| | Total | 18 | 0 | 0 | 0 | 0 | 115 | 299 |

§11 samples were exclude from the analysis
κ coefficient = 0.4526 (95% C.I. 37.45-53.07%)

3. Proof of Concept for Determining the Minimum DNA Quality Appropriate for PCR Using ddPCR Methods.

To improve the consistency of ddEGFR and cobas EGFR test, the minimum DNA quality suitable for PCR analysis was investigated by reanalyzing the ddEGFR data which provides the iQC copy number and iQC index (FIGS. 3 and 4).

The storage period of the FFPET blocks was reflected in the amount of amplifiable DNA, and the amount of amplifiable DNA in the samples aged 7-11 years decreased to less than 50% of the 1,000 GE (iQC index average=0.31, standard deviation, SD=0.57). In contrast, the amount of amplifiable DNA in the 2-6 year old samples was approximately 100% (iQC index=1.07, SD=0.69 average) (FIG. 5).

Hence, when FFPET was stored at room temperature, the iQC index decreased with storage period. The pattern of the DIN values of the 315 FFPET-DNA samples measured together was similar to the iQC copy number and index of those samples (FIG. 6).

4. Establishment of the iQC Index of ddEGFR Using FFPET Samples

As shown in FIG. 1, all of the 316 samples were classified into four groups according to the storage period, the DIN value, and the iQC copy number. First, the DIN values were analyzed for the 57 inconsistent samples among the 169 samples selected from the blocks stored for more than 6 years. 26 samples among the 147 samples whose block storage period was less then 6 years did not satisfy the DIN standard, and included in group 1. In order to set up the standard of iQC index, 60 inconsistent samples in group 1 were reanalyzed and the iQC index values of almost all the samples (58/60) were less than 0.5 (FIG. 8).

Based on these results, we set the sample selection standard as [block storage period≤6 years, DIN>2.5, iQC index≥0.5]. In addition, we confirmed a strong correlation between the ddEGFR iQC index and the DIN value, which proves that the iQC index indicates the quality of FFPET-DNA (Table 10).

TABLE 10

|  | iQC index | DIN Bad (<2.5) | DIN Good (>2.5) |
|---|---|---|---|
| Group 1 (n = 194) | Low (<0.5) | 155 | 2 |
| (p. < 0.0001) | High (≥0.5) | 22 | 15 |
| Group 2 (n = 113) | Low (<0.5) | 0 | 8 |
|  | High (≥0.5) | 0 | 113 |
| Group 3 (n = 150) | Low (<0.5) | 0 | 0 |
|  | High (≥0.5) | 22 | 128 |
| Group 4 (n = 166) | Low (<0.5) | 156 | 10 |
|  | High (≥0.5) | 0 | 0 |

5. Comparison of ddEGFR and Cobas EGFR Test Results According to the iQC Index Standard Satisfaction When the iQC index cut-off was applied to 121 samples (block storage period≤6 years, DIN>2.5), 113 samples remained (FIG. 1, group 2). Group 2 samples showed a very high agreement between ddEGFR and cobas EGFR assays (PPA=100.00%, NPA=76.00%, OPA=94.69%, κ=0.9197) (Table 11 and Table 12).

TABLE 11

| Pre-clinical study group | | cobas EG FR Test | | | | | |
|---|---|---|---|---|---|---|---|
| | | Group 2 | | | Group 3 | | |
| | | n = 113 | MD | MND | Total | n = 150 | MD | MND | Total |
| ddEGFR Test | MD | 88 | 6 | 94 | MD | 106 | 11* | 117 |
| | MND | 0 | 19 | 19 | MND | 0 | 33 | 33 |
| | Total | 88 | 25 | 113 | Total | 106 | 44 | 150 |
| PPA (95% C.I.) | | 100.0% (95.89-100.0%) | | | 100.0% (96.58-100.0%) | | |
| NPA (95% C.I.) | | 76.00% (54.87-90.64%) | | | 75.00% (59.66-86.81%) | | |
| OPA (95% C.I.) | | 94.69% (88.80-98.03%) | | | 92.67% (87.26-96.28%) | | |
| PPV (95% C.I.) | | 93.62% (86.62-97.62%) | | | 90.60% (83.80-95.21%) | | |
| NPV (95% C.I.) | | 100.0% (82.35-100.0%) | | | 100.0% (87.26-100.0%) | | |

TABLE 12

| Group 2 (n = 113) | | G719X | 19del | T790M | E20Ins | S768I | L858R | G719X, T790M | G719X, S768I | S768I, L858R | MND | Total |
|---|---|---|---|---|---|---|---|---|---|---|---|---|
| ddEGFR Test | G719X | 1 | | | | | | | | | 1 | 2 |
| | 19del | | 51 | | | | | | | | 1 | 52 |
| | T790M | | | 0 | | | | | | | | 0 |
| | E20Ins | | | | 0 | | | | | | 1 | 1 |
| | S768I | | | | | 0 | | | | | | 0 |
| | L858R | | | | | | 33 | | | | 3 | 36 |
| | G719X, T790M | | | | | | | 0 | | | | 0 |
| | G719X, S768I | | | | | | | | 2 | | | 2 |
| | S768I, L858R | | | | | | | | | 1 | | 1 |
| | MND | | | | | | | | | | 19 | 19 |
| | Total | 1 | 51 | 0 | 0 | 0 | 33 | 0 | 2 | 1 | 25 | 113 |

κ coefficient = 0.9197 (95% C.I. 85.85-98.09%)

To identify the clinical impact of the iQC index, we applied this standard to 316 FFPETs, classified 150 samples into group 3 (FIG. 1) and reanalyzed the agreement between the ddEGFR and the cobas EGFR results.

Similar to the results of Group 2 (all the standards applied), group 3 samples showed very high agreement rates (PPA=100.00%, NPA=75.00%, OPA=92.67%, κ=0.8923) (Table 11 and Table 13).

and cobas EGFR test (LoD of T790M=~3%, cobas EGFR v2). Based on the ddEGFR results of these three samples, the MI of T790M was ~1% (1.11%, 1.16% and 1.03%). In addition, 8 inconsistent samples were analyzed by Sanger, but no mutations were found (FIG. 10). In addition, microdissection was performed to enrich the tumor tissues, and subsequently EGFR mutations were reanalyzed in 8 samples

TABLE 13

| Group 3 (n = 150) | | cobas EGFR Test | | | | | | | | | | | |
|---|---|---|---|---|---|---|---|---|---|---|---|---|---|
| | | G719X | 19del | T790M | E20Ins | S768I | L858R | G719X, T790M | G719X, S768I | 19del, T790M | S768I, L858R | MND | Total |
| ddEGFR Test | G719X | 1 | | | | | | | | | | 1 | 2 |
| | 19del | | 61 | | | | | | | | | 1 | 62 |
| | T790M | | | 0 | | | | | | | | | 0 |
| | E20Ins | | | | 0 | | | | | | | 1 | 1 |
| | S768I | | | | | 0 | | | | | | | 0 |
| | L858R | | | | | | 41 | | | | | 4 | 45 |
| | G719X, T790M | | | | | | | 0 | | | | 1 | 1 |
| | G719X, S768I | | | | | | | | 2 | | | | 2 |
| | 19del, T790M | | 3 | | | | | | | 0 | | | 3 |
| | S768I, L858R | | | | | | | | | | 1 | | 1 |
| | MND | | | | | | | | | | | 33 | 33 |
| | Total | 1 | 64 | 0 | 0 | 0 | 41 | 0 | 2 | 0 | 1 | 41 | 150 |

κ coefficient = 0.8923 (95% C.I. 83.25-95.22%)

In contrast, group 4 samples that did not satisfy the iQC index standard showed very low agreement rates (PPA=78.57%, NPA=58.20%, OPA=63.41%, κ=0.3862) (Table 14).

Accordingly, the iQC index could be considered as a key factor determining whether the DNA is of sufficient quality for the ddEGFR test.

TABLE 14

| Group 4 | | cobas EGFR Test | | |
|---|---|---|---|---|
| (n = 166) | | MD | MND | Total |
| ddEGFR Test | MD | 33 | 51* | 84 |
| | MNS | 9 | 71 | 80 |
| | Total | 42 | 122 | 164 |
| PPA (95% C.I.) | | 78.57% (63.19-89.70%) | | |
| NPA (95% C.I.) | | 58.20% (48.93-67.06%) | | |
| OPA (95% C.I.) | | 63.41% (55.55-70.79%) | | |
| PPV (95% C.I.) | | 39.29% (28.80-50.55%) | | |
| NPV (95% C.I.) | | 88.75% (79.72-94.72%) | | |

1 sample: Invalid
*1 sample: cobas EGFR, 19del; ddEGFR, 19del/L858R
1 sample: cobas EGFR, E20Ins; ddEGFR, E20Ins/T790M
1 sample: cobas EGFR, S768I; ddEGFR, S768I/L858R 6. Analysis of Inconsistent Samples in the Preclinical Trial The iQC index standard was applied to reanalyze the remaining 11 inconsistent samples in Group 3. A schematic representation of the reanalysis workflow for the inconsistent sample is shown in FIG. 9. In three samples, the ddEGFR test showed a double mutation (19del/T790M), whereas cobas EGFR test and Sanger method showed only a single mutation (19del) (Table 11, group 3). This could result from the low detection sensitivity of Sanger (~15%) which generated negative results from cobas EGFR test, but positive results from ddEGFR test. Following the microdissection, cobas EGFR test generated the same results as ddEGFR test for 4 out of 8 samples (FIG. 10). Thus, the above results indicate that ddEGFR test is more sensitive in detecting EGFR mutations regardless of the tumor ratio. Aberrantly, there was one inconsistent case where a mutation (T790M/G719X) was detected in a preliminary analysis which was determined to be invalid by ddEGFR test after microdissection. Since the iQC index is very low (0.37, data not shown), DNA degradation might have happened during microdissection.

7. Clinical Trial for Retrospective Comparison of EGFR Tests

Next, the EGFR mutation status of 228 samples was analyzed using ddEGFR and cobas EGFR test; 57 samples were excluded based on the iQC index. The study design is shown in FIG. 3. The remaining 171 samples with iQC index≥0.5 had PPA of 98.23%, NPA of 82.76% and OPA of 92.98% between ddEGFR and cobas EGFR test (κ=0.9029, Table 15 and Table 16).

TABLE 15

| Retrospective comparison study, | | cobas EGFR Test | | |
|---|---|---|---|---|
| Applied iQC index (n = 171) | | MD | MND | Total |
| ddEGFR Test | MD | 111 | 10* | 121 |
| | MND | 2 | 48 | 50 |
| | Total | 113 | 58 | 171 |
| PPA (95% C.I.) | | 98.23% (93.75-99.78%) | | |
| NPA (95% C.I.) | | 82.76% (70.57-91.41%) | | |
| OPA (95% C.I.) | | 92.98% (88.06-96.32%) | | |

TABLE 15-continued

| Retrospective comparison study, | cobas EGFR Test | | |
|---|---|---|---|
| Applied iQC index (n = 171) | MD | MND | Total |
| PPV (95% C.I.) | 91.74% (85.33-95.97%) | | |
| NPV (95% C.I.) | 96.00% (86.29-99.51%) | | |

TABLE 16

| | | cobas EGFR Test | | | | | | | | | | | | |
|---|---|---|---|---|---|---|---|---|---|---|---|---|---|---|
| Applied IQC Index (n = 171) | | G719X | 19del | T790M | E20Ins | S768I | L858R | L861Q | 19del, T790M | G719X, S768I | G719X, L858R | G719X, L861 | T790M, L858R | MND | Total |
| ddEGFR Test | G719X | 2 | | | | | | | | | | | | | 2 |
| | 19del | | 46 | | | | | | | | | | | | 46 |
| | T790M | | | 0 | | | | | | | | | | | 0 |
| | E20Ins | | | | 2 | | | | | | | | | 1 | 3 |
| | S768I | | | | | 0 | | | | | | | | | 0 |
| | L858R | | | | | | 54 | | | | | | | 2 | 56 |
| | L861Q | | | | | | | 0 | | | | | | 1 | 1 |
| | 19del, T790M | | 3 | | | | | | 1 | | | | | | 4 |
| | G719X, S768I | | | | | | | | | 3 | | | | | 3 |
| | G719X, L858R | | | | | | 1 | | | | 0 | | | | 1 |
| | G719X, L861Q | 1 | | | | | | | | | | 0 | | | 1 |
| | T790M, L858R | | | | | | 1 | | | | | | 3 | | 4 |
| | MND | | 2 | | | | | | | | | | | 48 | 50 |
| | Total | 3 | 51 | 0 | 2 | 0 | 56 | 0 | 1 | 3 | 0 | 0 | 3 | 52 | 171 |

κ coefficient = 0.9029 (95% C.I. 85.08-95.49%)

Double mutations were detected by ddEGFR test in the 6 samples out of 12 inconsistent samples, whereas only a single mutation was detected by cobas EGFR test. As expected, the MIs of additionally detected mutations were very low. One inconsistent case was a mutation (L861Q) which was not detected by cobas EGFR test, but was detected in both ddEGFR and Sanger method. In contrast, another inconsistent case was a mutation (19 del) which was not found with ddEGFR test, but discovered by cobas EGFR test and Sanger method. This was an uncommon mutation of the 19del subtype (c.2239_2264del_insGCGAA) resulting from a non-specific response, not designed in cobas EGFR assay, therefore it could not be used to distinguish a potentially false detection and a beneficial cross-reaction of the commercial diagnostic kit.

In addition, DIN values were measured from 228 FFPET-DNA samples and a pattern similar to the iQC index was observed. Furthermore, most recent samples (within one year) had values of DIN>2.5 and iQC index≥0.5 (FIG. 11). These data support that the iQC index is a very strong indicator of the quality of FFPET-DNA. These results also demonstrate that ddEGFR assay is a robust diagnostic tool for the accurate detection of EGFR mutations in the clinical settings.

As noted above, the poor quality of FFPET-DNA and subsequent changes in the mutation status can lead to a misdiagnosis. Therefore, much effort is required to optimize the sample standards to determine the quality of FFPET-DNA suitable for PCR. In the present invention, the iQC index standard was established to determine the minimum quality of FFPET-DNA and benefits of applying these criteria in clinical practice were verified.

In this embodiment of the present invention, the present inventors found that an automated tissue preparation system (TPS, Siemens Healthcare, Erlangen, Germany) which can minimize handling errors and reduce the effects of formaldehyde-induced DNA-DNA and DNA-protein crosslinkings, and Uracil-DNA glycosylase (UDG) treatments were all powerful strategy to reduce false-positive results due to sequence artifacts. However, it has also been shown that sequence artifacts due to DNA fragmentation may still be a problem. Depending on the degree of DNA fragmentation, the same amount of DNA obtained from the different FFPET samples can contain a significantly different amount of amplifiable DNA templates. For these reasons, PCR-based methods such as qPCR, ddPCR and next generation sequencing (NGS) may be suitable for quantifying the amount of amplifiable templates in the FFPET-DNA.

In addition, the present inventors have found that the iQC copy numbers can be used as an indicator of the concentration of input DNA, and a new concept of mutation defined as mutation index (MI) can be used as an index of mutation level reflecting DNA quality. MI can provide more accurate information regarding mutation levels than the mutation frequency simply calculated based on the input DNA concentrations.

The concept of iQC index according to the present invention described above is summarized in FIG. 12, and the concept of MI is summarized in FIG. 13.

INDUSTRIAL APPLICABILITY

According to the methods of the present invention, it is possible to objectively evaluate the nucleic acid quality in a biological sample used for gene analysis and to provide objective results about the frequency of genetic mutations, therefore it is effective in providing reliable information in the fields of clinical research and companion diagnostics, and industrial applicability is very high.

What is claimed is:

1. A method for selecting a nucleic acid from a biological sample which provides a reliable gene analysis result, the method comprising the steps of:
   (a) extracting a nucleic acid from a biological sample obtained from a subject;
   (b) performing digital Polymerase Chain Reaction (PCR) on the extracted nucleic acid with i) primers or ii) a set of primers and a probe which are capable of amplifying an internal quality control region in the extracted nucleic acid, wherein the internal quality control region is located at a site adjacent to and within 20 kilobases (kb) of a target gene or a gene comprising a mutation site in the extracted nucleic acid;
   (c) calculating a copy number of the internal quality control region from the result of the digital PCR;
   (d) calculating an internal quality control index (iQC index) according to the following equation:

Internal quality control index=the copy number of the internal quality control region/the copy number of input DNA of the digital PCR; and (e) determining that the nucleic acid quality of the sample is appropriate in case where the internal quality control index is equal to or higher than a predetermined threshold, or determining that the nucleic acid quality of the sample is better as the internal control quality index becomes closer to 1; and
   (f) selecting a nucleic acid from the biological sample for a reliable gene analysis in accordance with the nucleic acid quality as determined quantitatively in step (e);
   wherein the nucleic acid quality of the sample is determined to detect or analyze the integrity of the target gene or the gene comprising the mutation site as an amplifiable template in the sample; and
      wherein a detected copy number of the internal quality control region/the copy number of input DNA of the reference standard is 0.90 to 1.10 in case where the primers are subjected to quantitative digital PCR on a reference standard material of which copy number of the internal quality control region is known.

2. The method of claim 1, wherein the biological sample is at least one selected from the group consisting of a cell line, a histological slide, a biopsy sample, a formalin-fixed paraffin-embedded (FFPE) tissue, a body fluid, feces, urine, plasma, serum, whole blood, isolated blood cells, and cells isolated from blood.

3. The method of claim 1, wherein the internal quality control region is one or more regions.

4. The method of claim 1, wherein the threshold value is selected from the group consisting of 0.3, 0.4, 0.5, 0.6, 0.7, 0.8, 0.9, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.89, and 0.90.

5. The method of claim 1, wherein the nucleic acid quality is appropriate for an analysis selected from the group consisting of real-time PCR, digital PCR, genome sequencing, pyrosequencing, and next generation sequencing.

6. A method for preparing i) primers or ii) a set of primers and a probe for selecting a nucleic acid from a biological sample which provides a reliable gene analysis result, the method comprising the steps of:
   (a) designing i) primers or ii) a set of primers and a probe which are capable of amplifying a nucleic acid fragment of an internal quality control region in a nucleic acid extracted from a biological sample of a subject, wherein the internal quality control region is located at a site adjacent to and within 20 kilobases (kb) of a target gene or a gene comprising a mutation site in the extracted nucleic acid;
   (b) performing digital Polymerase Chain Reaction (PCR) on a nucleic acid contained in a reference standard material with the primers or the set of the primers and the probe;
   (c) calculating a copy number of the internal quality control region from the result of the digital PCR;
   (d) evaluating the copy number of the internal quality control region detected/the copy number of input DNA of the reference standard substance of the designed primers or the designed set of the primers and the probe; and (e) selecting primers or a set of primers and a probe of which the copy number of the internal quality control region detected/the copy number of input DNA of the reference standard substance is quantitatively determined as 0.90 to 1.10, as primers or a set of primers and a probe for selecting a nucleic acid from a biological sample which provides a reliable gene analysis result.

7. The method of claim 6, wherein the step (e) comprises selecting a primer of which the copy number of the internal quality control region detected/the copy number of input DNA of the reference standard substance is 0.95 to 1.15.

8. A method for selecting a nucleic acid from a biological sample which provides a reliable gene analysis result, the method comprising the steps of:
   (a) extracting a nucleic acid from a biological sample obtained from a subject;
   (b) performing a first digital Polymerase Chain Reaction (PCR) on the extracted nucleic acid with i) primers or ii) a set of primers and a probe which are capable of amplifying an internal quality control region in the extracted nucleic acid, wherein the internal quality control region is located at a site adjacent to and within 20 kilobases (kb) of a target gene or a gene comprising a mutation site in the extracted nucleic acid;
   (c) calculating a copy number of the internal quality control region from the result of the first digital PCR;
   (d) performing a second digital Polymerase Chain Reaction (PCR) on the extracted nucleic acid with iii) primers or iv) a set of primers and a probe which are capable of amplifying a target gene or mutation site;
   (e) calculating the copy number of the target gene or the mutation site from the result of the second digital PCR; and
   (f) calculating a % mutation index according to the following equation:

% mutation index=the copy number of the target gene or mutation site/the copy number of the internal quality control region×100; and (g) selecting a nucleic acid from the biological sample for a reliable gene analysis in accordance with the % mutation index as determined quantitatively in step (f);
   wherein a detected copy number of the internal quality control region/the copy number of input DNA of the reference standard substance is 0.90 to 1.10 in case where the primers are subjected to quantitative digital PCR on a reference standard material of which copy number of the internal quality control region is known.

9. A method for selecting a nucleic acid from a biological sample which provides a reliable gene analysis result, the method comprising the steps of:
   (a) measuring the mutational frequency of a target gene or a mutation site in a biological sample; and
   (b) calculating a normalized mutation frequency by dividing the measured mutation frequency by an internal quality control index of the sample,
   wherein the internal quality control index (iQC index) is calculated in a method comprising the steps of:
      (i) extracting a nucleic acid from a biological sample obtained from a subject;
      (ii) performing digital Polymerase Chain Reaction (PCR) on the extracted nucleic acid with i) primers or ii) a set of primers and a probe which are capable of amplifying a nucleic acid fragment of an internal quality control region;
      (iii) calculating a copy number of the internal quality control region from the result of the digital PCR; and
      (iv) calculating the internal quality control index (iQC index) according to the following equation:

Internal quality control index=the copy number of internal quality control region/the copy number of input DNA of the digital PCR; and (c) selecting a nucleic acid from the biological sample for a reliable gene analysis in accordance with the mutational frequency of a target gene or a mutation site as determined quantitatively in step (b);
   wherein the internal quality control region in a nucleic acid extracted from the biological sample is located at a site adjacent to and within 20 kilobases (kb) of a target gene or a gene comprising a mutation site in the extracted nucleic acid; and
   wherein a detected copy number of the internal quality control region/the copy number of input DNA of the reference standard substance is 0.90 to 1.10 in case where the primers are subjected to quantitative digital PCR on a reference standard material of which copy number of the internal quality control region is known.

* * * * *